US008962256B2

US008962256B2

(12) United States Patent
Kachurin et al.

(10) Patent No.: US 8,962,256 B2
(45) Date of Patent: Feb. 24, 2015

(54) SURFACE-ASSISTED HEMAGGLUTINATION AND HEMAGGLUTINATION INHIBITION ASSAYS

(75) Inventors: Anatoly Kachurin, Orlando, FL (US); Vaughan Wittman, Oviedo, FL (US); Mike N. Nguyen, Orlando, FL (US); Olga Kachurina, Orlando, FL (US); Tenekua Tapia, Orlando, FL (US); Vipra Dhir, Orlando, FL (US); Alexander Karol, Orlando, FL (US)

(73) Assignee: Sanofi Pasteur Vaxdesign Corp., Orlando, FL (US)

( * ) Notice: Subject to any disclaimer, the term of this patent is extended or adjusted under 35 U.S.C. 154(b) by 912 days.

(21) Appl. No.: 12/908,211

(22) Filed: Oct. 20, 2010

(65) Prior Publication Data

US 2011/0097705 A1 Apr. 28, 2011

Related U.S. Application Data

(60) Provisional application No. 61/253,266, filed on Oct. 20, 2009.

(51) Int. Cl.
*G01N 33/53* (2006.01)
*G01N 33/555* (2006.01)
*G01N 33/569* (2006.01)
*G01N 33/543* (2006.01)

(52) U.S. Cl.
CPC .... *G01N 33/56983* (2013.01); *G01N 33/54353* (2013.01); *G01N 33/54393* (2013.01); *G01N 33/555* (2013.01)
USPC .......................................... 435/7.1; 435/366

(58) Field of Classification Search
None
See application file for complete search history.

(56) References Cited

U.S. PATENT DOCUMENTS

| 4,921,787 | A | 5/1990 | Riggin |
| 5,494,800 | A | 2/1996 | Smith |
| 5,583,004 | A | 12/1996 | Pincus |
| 2009/0325148 | A1 * | 12/2009 | Kachurin et al. ................ 435/5 |

FOREIGN PATENT DOCUMENTS

| EP | 0015841 | 9/1980 |
| WO | 95/02186 | 1/1995 |
| WO | 2010002852 | 1/2010 |

OTHER PUBLICATIONS

Yamamoto et al. Development of a particle agglutination assay system for detecting Japanese encephalitis virus-specific human IgM, using hydroxyapatite-coated nylon beads. Journal of Virological Methods, 2002, vol. 104, p. 195-201.*

Riquelme et al. Study of polycation effects on erythrocyte agglutination mediated by anti-glycophorins using microscopic image digital analysis. Biophotonics and New Therapy Frontiers, 2006, vol. 6191, p. 61911G-61910G.*
Chapagain, Moti L. et al., Comparison of real-time PCR and hemagglutination assay for quantitation of human polyomavirus JC, Virology Journal, 3:3, pp. 1-5 (2006).
Cross, Garry et al., Hemagglutination Inhibition Assays, Seminars in Avian and Exotic Pet Medicine, vol. 11, No. 1, pp. 15-18, (2002).
Fujino, Motoko et al., Development of a new neutralization test for measles virus, Journal of Virological Methods 142:15-20 (2007).
Hatgi, John N. et al., Immunological Studies With Group B Arthropod-Borne Viruses VI. Hemagglutination-Inhibiting Antibody Responses to 17D Yellow Fever Vaccine in Human Subjects With Different Degrees of Complexity of Pre-Vaccination Group B Virus Experiences, American Journal of Tropical Medicine and Hygiene, vol. 16, No. 4, pp. 601-610 (1966).
Hierholzer, John C., Standardized Viral Hemagglutination and Hemagglutination-Inhibition Tests II. Description and Statistical Evaluation, Applied Microbiology, 18(5):824-833 (1969).
Hubby, Bolyn et al., Development and preclinical evaluation of an alphavirus replicon vaccine for influenza, Vaccine 25:8180-8189 (2007).
Ko, KH et al., A latex slide agglutination test for rapid detection of antimyeloperoxidase antibody, Journal of Clincal Pathology, 1999, v. 52 n. 10, p. 770-772.
Niedrig, M. et al., Assessment of IgG antibodies against yellow fever virus after vaccination with 17D by different assays: neutralization test, haemagglutination inhibition test, immunofluorescence assay and ELISA, Tropical Medicine and International Health, Dec. 1999, vol. 4 No. 12, pp. 867-871.
Noah, Diana L., Qualification of the Hemagglutination Inhibition Assay in Support of Pandemic Influenza Licensure, Clinical and Vaccine Immunology, 16(4):558-566 (2009).
Salk, Jonas E., A Simplified Procedure for Titrating Hemagglutinating Capacity of Influenza-Virus and the Corresponding Antibody, From the Department of Epidemiology and the Virus Laboratory, J. Immunology 49:84-98 (1944).

(Continued)

*Primary Examiner* — Stacy B Chen
(74) *Attorney, Agent, or Firm* — Roylance, Abrams, Berdo & Goodman, L.L.P.

(57) ABSTRACT

Hemagglutination (HA) and hemagglutination inhibition (HAI) functional assays remain important instruments of analysis of virus-cell interaction and protecting efficacy of virus-specific antibodies and sera. However, they demonstrate limited sensitivity towards many viruses, and require significant volumes of viruses, erythrocytes, sera, and antibodies. The present invention comprises new and significantly more sensitive versions of the HA and HAI assays based on observing agglutination on activated surfaces of specifically opsonized plates and ELISA plates rather than in solution. A version of the new assay that uses ELISA plates additionally allows characterizing the affinity of functional antibodies in the tested sera and fluids, which is not possible in the classical HAI assay. The methods of the present invention can also be used to improve the sensitivity of agglutination methods based on latex beads and to develop agglutination methods using target cells other than erythrocytes.

17 Claims, 25 Drawing Sheets

(56) References Cited

OTHER PUBLICATIONS

Wang, Shixia et al., Heterologous HA DNA vaccine prime-inactivated influenza vaccine boost is more effective than using DNA or inactivated vaccine alone in eliciting antibody responses against H1 or H3 serotype influenza viruses, Vaccine, 26(29-30):3626-33 (2008).

WHO Manual on Animal Influenza Diagnosis and Surveillance, World Health Organization, Department of Communicable Disease Surveillance and Response, pp. 1-98 (2002).

Xu, Xiaojuan et al., Latex Agglutination Test for Monitoring Antibodies to Avian Influenza Virus Subtype H5N1, Journal of Clincal Microbiology, Apr. 2005, p. 1953-1955, vol. 43, No. 4.

Int'l Search Report for PCT/US2010/53322, dated Jun. 23, 2011.

Supplementary European Search Report dated Nov. 27, 2013 for EP Patent Application No. 10825569.6.

* cited by examiner

Figure 5C

C

|   | 1 | 2 | 3 | 4 | 5 | 6 | 7 | 8 | 9 | 10 | 11 | 12 |
|---|---|---|---|---|---|---|---|---|---|---|---|---|
| A | 174 | 162 | 301 | 350 | 122 | 117 | 175 | 143 | 114 | 117 | 146 | 148 |
| B | 266 | 159 | 264 | 275 | 121 | 142 | 169 | 186 | 123 | 115 | 125 | 110 |
| C | 308 | 199 | 359 | 319 | 114 | 134 | 265 | 213 | 142 | 170 | 125 | 143 |
| D | 500 | 369 | 424 | 409 | 133 | 100 | 424 | 466 | 192 | 193 | 189 | 244 |
| E | 482 | 560 | 556 | 570 | 125 | 117 | 473 | 557 | 389 | 319 | 283 | 267 |
| F | 591 | 631 | 578 | 589 | 185 | 178 | 571 | 561 | 520 | 428 | 533 | 513 |
| G | 594 | 592 | 571 | 579 | 350 | 403 | 607 | 578 | 578 | 575 | 566 | 552 |
| H | 561 | 612 | 567 | 589 | 556 | 532 | 586 | 589 | 590 | 607 | 602 | 573 |

Linked HAP (E11, E12: 283, 267)

Figure 7:
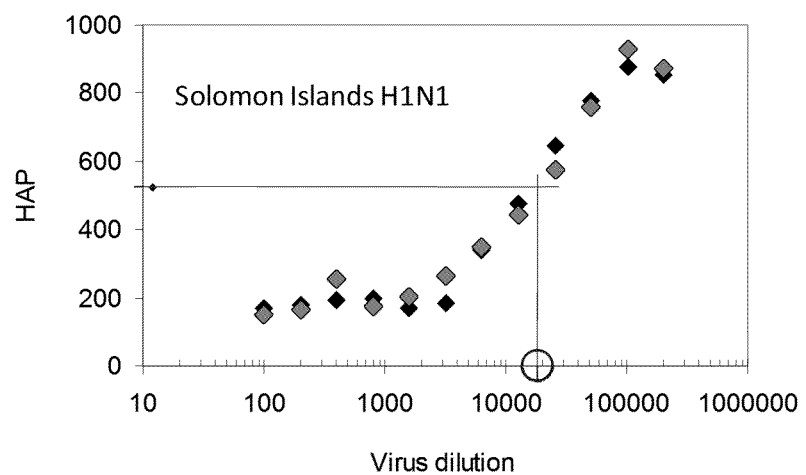

Dataset table to Figure 7

| Virus dilution | HAP 1 | HAP 2 |
|---|---|---|
| 100 | 171.1 | 150.2 |
| 200 | 177.4 | 167.0 |
| 400 | 193.0 | 255.0 |
| 800 | 197.4 | 175.7 |
| 1600 | 169.5 | 204.4 |
| 3200 | 182.4 | 262.9 |
| 6400 | 340.9 | 348.3 |
| 12800 | 475.6 | 441.1 |
| 25600 | 647.3 | 573.5 |
| 51200 | 778.9 | 761.1 |
| 102400 | 876.2 | 928.1 |
| 204800 | 852.3 | 874.8 |

Figure 9B

Figure 9A:
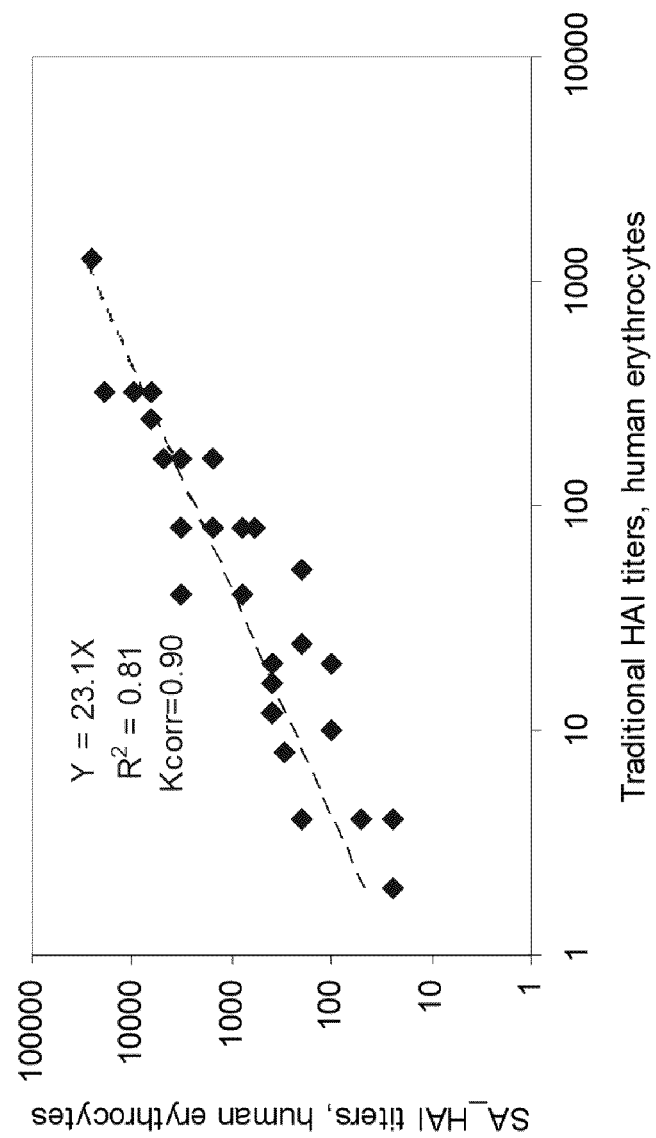

Dataset table to Figure 9.

| Donor # | Pre/post | HAI | SA_HAI | Titer ratio |
|---|---|---|---|---|
| 71 | Pre- | 40 | 3200 | 80.0 |
|  | Post- | 80 | 3200 | 40.0 |
| 91 | Pre- | 4 | 200 | 50.0 |
|  | Post- | 16 | 400 | 25.0 |
| 102 | Pre- | 8 | 300 | 37.5 |
|  | Post- | 80 | 800 | 10.0 |
| 138 | Pre- | 4 | 25 | 6.3 |
|  | Post- | 80 | 1600 | 20.0 |
| 145 | Pre- | 24 | 200 | 8.3 |
|  | Post- | 160 | 3200 | 20.0 |
| 146 | Pre- | 2 | 25 | 12.5 |
|  | Post- | 80 | 600 | 7.5 |
| 182 | Pre- | 12 | 400 | 33.3 |
|  | Post- | 80 | 3200 | 40.0 |
| 184 | Pre- | 52 | 200 | 3.8 |
|  | Post- | 240 | 6400 | 26.7 |
| 196 | Pre- | 20 | 400 | 20.0 |
|  | Post- | 160 | 4800 | 30.0 |
| 208 | Pre- | 4 | 50 | 12.5 |
|  | Post- | 160 | 1600 | 10.0 |
| 355 | Pre- | 160 | 3200 | 20.0 |
|  | Post- | 320 | 19400 | 60.6 |
| 419 | Pre- | 20 | 100 | 5.0 |
|  | Post- | 1250 | 25600 | 20.5 |
| 497 | Pre- | 20 | 100 | 5.0 |
|  | Post- | 160 | 3200 | 20.0 |
| 608 | Pre- | 40 | 800 | 20.0 |
|  | Post- | 320 | 9600 | 30.0 |
| 653 | Pre- | 10 | 100 | 10.0 |
|  | Post- | 320 | 6400 | 20.0 |
|  |  |  |  |  |
|  |  |  | Average | 23.5 |

Figure 10B

Figure 10A:
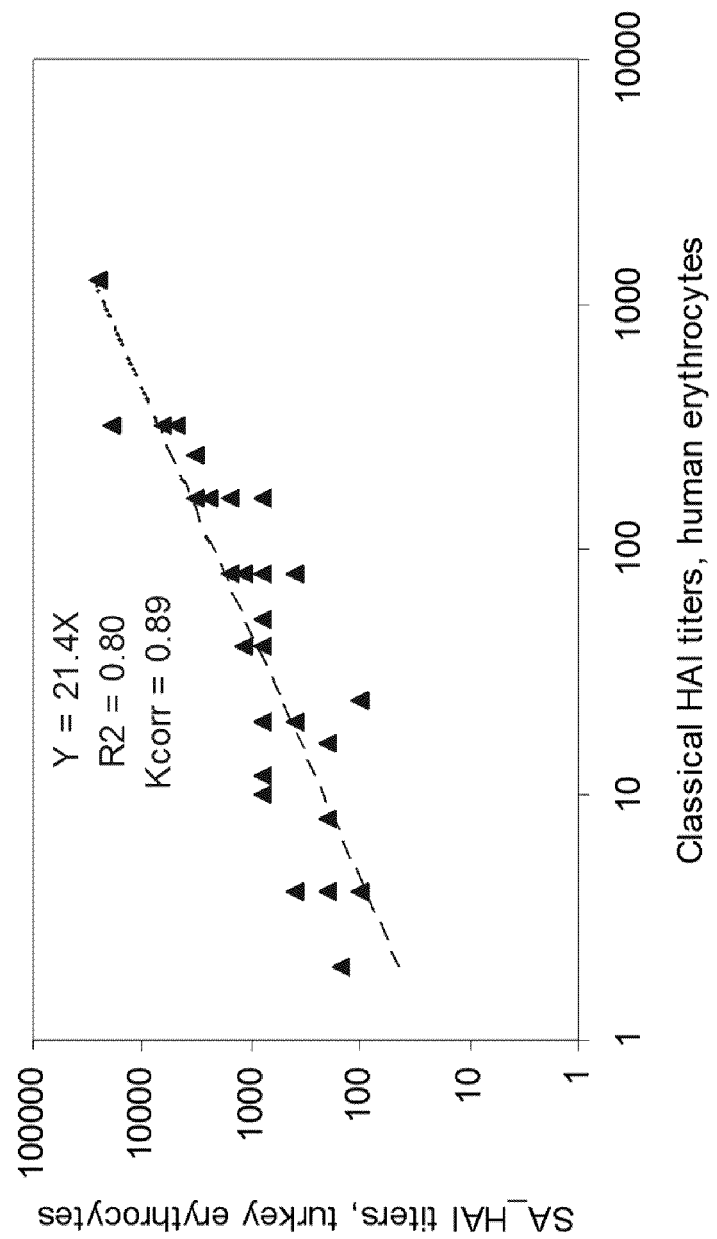

Dataset table to Figure 10.

| Donor # | Pre/post | HAI | SA_HAI | Titer ratio |
|---|---|---|---|---|
| 71 | Pre- | 40 | 1200 | 30.0 |
|  | Post- | 80 | 1600 | 20.0 |
| 91 | Pre- | 4 | 100 | 25.0 |
|  | Post- | 16 | 200 | 12.5 |
| 102 | Pre- | 8 | 200 | 25.0 |
|  | Post- | 80 | 400 | 5.0 |
| 138 | Pre- | 4 | 200 | 50.0 |
|  | Post- | 80 | 800 | 10.0 |
| 145 | Pre- | 24 | 100 | 4.2 |
|  | Post- | 160 | 1600 | 10.0 |
| 146 | Pre- | 2 | 150 | 75.0 |
|  | Post- | 80 | 400 | 5.0 |
| 182 | Pre- | 12 | 800 | 66.7 |
|  | Post- | 80 | 1200 | 15.0 |
| 184 | Pre- | 52 | 800 | 15.4 |
|  | Post- | 240 | 3200 | 13.3 |
| 196 | Pre- | 20 | 400 | 20.0 |
|  | Post- | 160 | 3200 | 20.0 |
| 208 | Pre- | 4 | 400 | 100.0 |
|  | Post- | 160 | 800 | 5.0 |
| 355 | Pre- | 160 | 2400 | 15.0 |
|  | Post- | 320 | 19400 | 60.6 |
| 419 | Pre- | 20 | 400 | 20.0 |
|  | Post- | 1250 | 25600 | 20.5 |
| 497 | Pre- | 20 | 800 | 40.0 |
|  | Post- | 160 | 3200 | 20.0 |
| 608 | Pre- | 40 | 800 | 20.0 |
|  | Post- | 320 | 6400 | 20.0 |
| 653 | Pre- | 10 | 800 | 80.0 |
|  | Post- | 320 | 4800 | 15.0 |
|  |  |  |  |  |
|  |  |  | Average | 27.9 |

Figure 11:
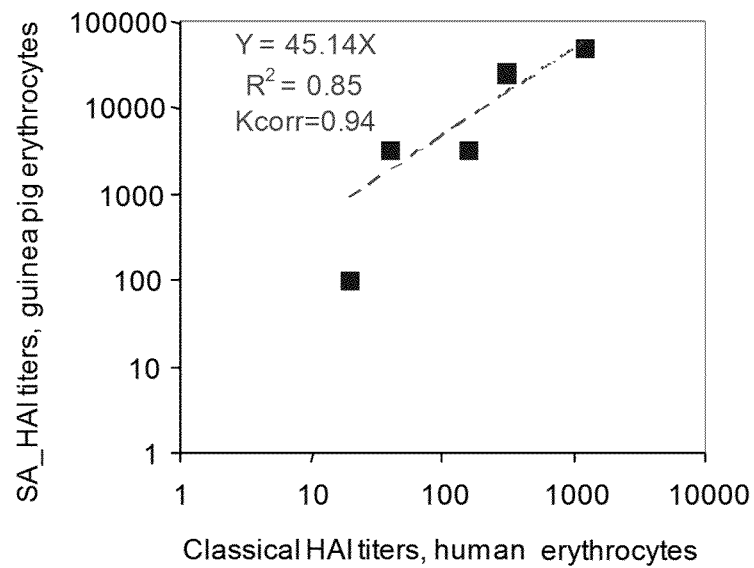

Dataset table to Figure 11

| Donor # | Pre/Post | HAI | SA_HAI | Titer ratio |
|---|---|---|---|---|
| 355 | Pre- | 160 | 3200 | 20.0 |
|  | Post- | 320 | 25600 | 80.0 |
| 419 | Pre- | 20 | 100 | 5.0 |
|  | Post- | 1250 | 51200 | 41.0 |
| 608 | Pre- | 40 | 3200 | 80.0 |
|  | Post- | 320 | 25600 | 80.0 |
|  |  |  |  |  |
|  |  |  | Average | 51.0 |

Figure 12A & B

Figure 12C

Dataset table to Figure 12.

| Virus | Classical HA assay | SA-HA assay | HA sensitivity enhancement |
|---|---|---|---|
| A/Brisbane/59/2007 (H1N1) | 1502 | 49020 | 32.6 |
| A/Solomon Islands/3/2006 (H1N1) | 831 | 27040 | 32.5 |
| A/New Caledonia/20/99 (H1N1) | 1199 | 7880 | 6.6 |
| A/Wisconsin/67/2005 (H3N2) | 462 | 3470 | 7.5 |
| B/Malaysia/2506/2004 | 518 | 32500 | 62.7 |
| B/Florida/4/2006 | 79 | 15998 | 202.5 |

Figure 13:
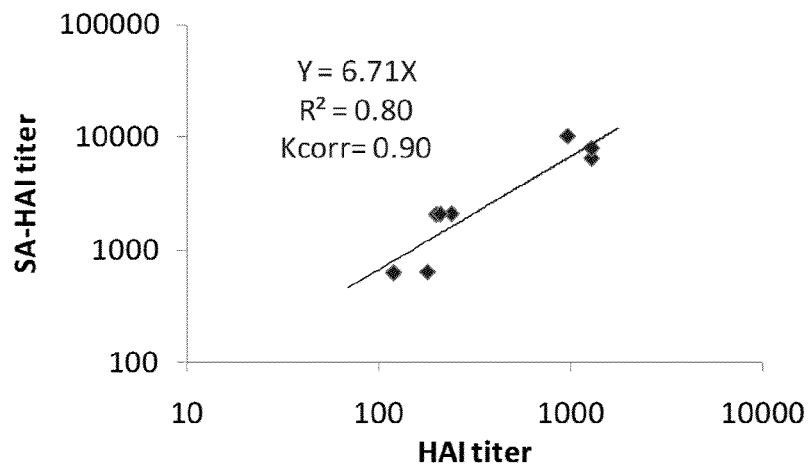

Dataset table to figure 13

| Serum # | HAI | SA-HAI | Titer ratio |
|---|---|---|---|
| 214 | 1280 | 6400.0 | 5.0 |
| 82 | 960 | 10050.0 | 10.5 |
| 346 | 1280 | 7872.5 | 6.2 |
| 22 | 200 | 2050.0 | 10.3 |
| 43 | 180 | 636.2 | 3.5 |
| 52 | 240 | 2080.5 | 8.7 |
| 71 | 210 | 2063.8 | 9.8 |
| 184 | 120 | 628.6 | 5.2 |
| 258 | 120 | 625.0 | 5.2 |
|  |  |  |  |
| Average |  |  | 7.1 |

Figure 14:
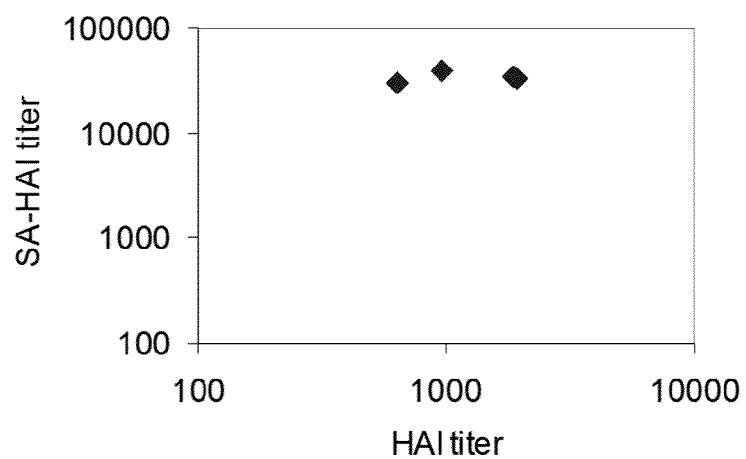

Dataset table to Figure 14

| Serum # | HAI | SA-HAI | Titer ratio |
|---|---|---|---|
| 72 | 1920.0 | 32500.0 | 16.9 |
| 114 | 1880.0 | 34176.8 | 18.2 |
| 214 | 960.0 | 39925.0 | 41.6 |
| 260 | 640.0 | 30020.0 | 46.9 |
|  |  |  |  |
| Average |  |  | 30.9 |

Figure 16

Figure 17
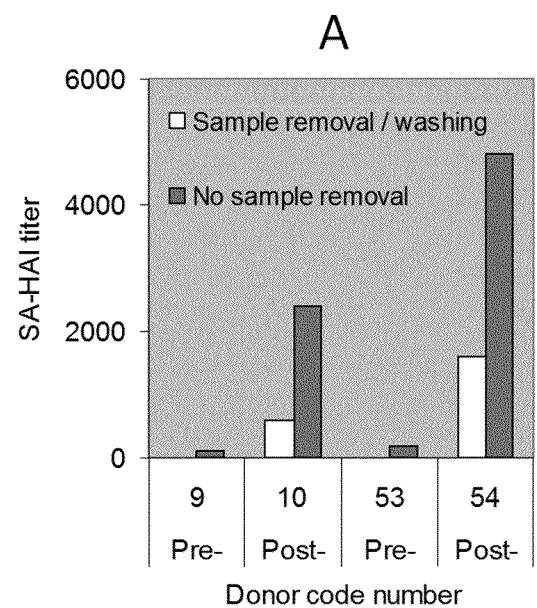
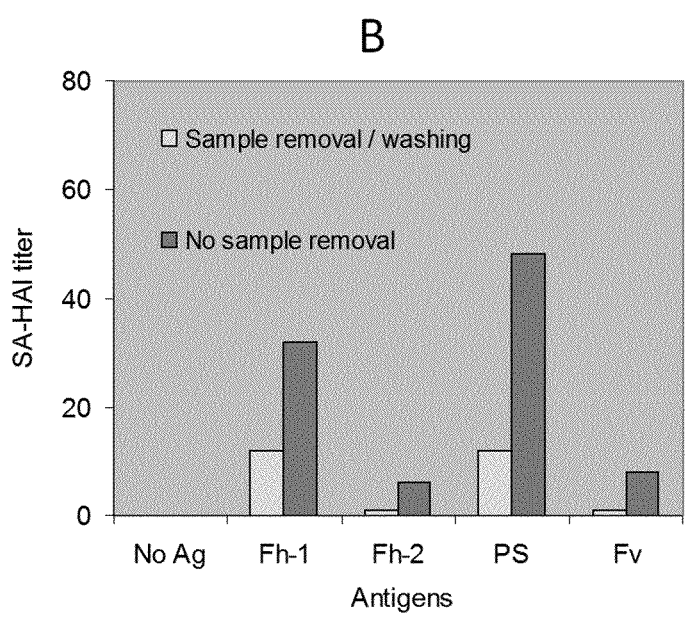

ilities of the anti-viral immunization, and for studying the
SURFACE-ASSISTED HEMAGGLUTINATION AND HEMAGGLUTINATION INHIBITION ASSAYS

CROSS-REFERENCE TO RELATED APPLICATIONS

This application claims benefit under 35 U.S.C. §119(e) of U.S. Patent Application No. 61/253,266, filed Oct. 20, 2009, which is hereby incorporated herein by reference in its entirety.

BACKGROUND TO THE INVENTION

Hemagglutinin proteins expressed on the surface of many viruses, such as influenza, rubella, smallpox, and others, agglutinate red blood cells (erythrocytes). This effect provides the basis for virus titration using hemagglutination (HA) assays. Specific attachment of antibodies to epitopes of the hemagglutinins responsible for attachment to the erythrocytes blocks binding of the virus particles to erythrocytes. This effect provides the basis for hemagglutination inhibition (HAI or HI) assays.

Hemagglutination assays and hemagglutination inhibition assays were introduced into medical and virology practice more than 60 years ago (Salk (1944) J. Immunol. 49, 87-98). Since that time, they have become important tools for measuring concentrations and strengths of viral cultures, the efficacy of the anti-viral immunization, and for studying the neutralizing capacity of virus-specific antibodies.

Two decades later, attempts were made to develop the method to a universal standard (Hierholzer et al. (1969) Applied Microbiol. 18, 824-833). However, the protocol for HAI assays kept undergoing minor modifications (e.g., Cross (2002) Seminars in Avian and Exotic Pet Medicine 11, 15-18; Hubby et al. (2007) Vaccine 25, 8180-8189; Wang et al. (2008) Vaccine 26 3626-3633; Noah et al. (2009), Clinical and Vaccine Immunology 16, 558-566), while preserving the core elements intact: observation of the agglutination in the solution volume, and visual detection of hemagglutination or hemagglutination inhibition.

In classical HA/HAI assays, the antigen (e.g., live or inactivated virus), either as is, or pre-incubated with an anti-serum or antibody of interest, is mixed with a suspension of purified erythrocytes, such as human group O erythrocytes, or avian, equine, or murine erythrocytes, depending on the type of the virus and objective of the study. After incubation of the mixture in V- or U-bottomed microwells, the major visual effect can be two-fold:

If antiserum is absent or unable to effectively block the attachment of the virus to erythrocytes, the virus particles link the erythrocytes into a dispersed three-dimensional semi-transparent gel, referred to as a "halo."

If the virus is effectively blocked or absent, then the erythrocytes precipitate to the bottom of the well, forming the characteristic bright pellet, or "button."

Using avian erythrocytes, the agglutination effect can be observed (optionally) by inability of the agglutinated erythrocytes to flow down the V-surface of the tilted plates.

To determine the concentration or strength of a viral culture in the HA hemagglutination assay, the sample is subjected to two-fold serial dilutions, until the agglutination vanishes. To determine the efficacy of the antiserum or tested antibody in the HAI assay, the serum sample is similarly subjected to serial dilution, until agglutination appears. The last dilution on the "borderline" between agglutination/non-agglutination is called the HA or HAI titer.

HA and HAI assays are used for the study of immune response to a multitude of different pathogenic viruses, including adenoviruses, enteroviruses, reoviruses, myxoviruses, poxviruses, and flaviviruses, which cause a wide spectrum of human and animal illnesses, from influenza and rubella to smallpox and Dengue hemorrhagic fever (e.g., Hatgi et al. (1966) Am. J. Trop. Med. Hyg. 15, 601-610; Hierholzer et al. (1969) Applied Microbiol. 18, 824-833; Cross (2002) Seminars in Avian and Exotic Pet Medicine 11, 15-18; Hubby et al. (2007) Vaccine 25, 8180-8189; Wang et al. (2008) Vaccine 26, 3626-3633). Thus, HA and HAI tests remain major tools in modern virology (WHO Manual on Animal Influenza Diagnosis and Surveillance, WHO/CDS/CSR/NCS2002.5 Rev. 1.). Significant improvements to the assays could be of widespread benefit.

The virtues of HA/HAI assays, based on erythrocytes, inspired the development of various versions of agglutination/agglutination inhibition tests, based on latex microbeads coated with various antigens and affinity ligands, including hemagglutinins and virus particles (Ko et al. (1999), J. Clin. Pathol. 52, 770-772; Xu et al. (2005), J. Clin. Microbiol., 43, 1953-1955). These methods, although fast and reliable, do not provide greater sensitivity to sera or antibody solutions than the classical HAI.

An objective of the invention presented here was the development of a functional assay of enhanced sensitivity that would use real target cells (e.g., erythrocytes), rather than synthetic particles, and would stay as close as possible to the well-proven and widely accepted classical HA/HAI. On the other hand, basic principles illustrated in embodiments of the current invention could be applied to latex bead agglutination methods to increase their sensitivity and informational capacity.

While robust, uncomplicated and reliable, HA and HAI assays lack adequate sensitivity in the cases of some conditions, such as measles, yellow fever, and polyoma (Chapagain et al. (2006) Virology J, 3, 3-5; Fujino et al. (2007) J. Virological Methods 142, 15-20; Niedrig et al. (1999) Trop. Med. Int. Health 4, 67-71). Further, assessments of agglutination are typically performed by the human eye, which can become a source of subjective evaluation.

In addition to the inadequate sensitivity of the standard HA/HAI assays with many viruses, as mentioned above, the development of modern in vitro systems for high-throughput analysis of immune responses, such as the MIMIC® system, described in US 2005/0282148, required improved sensitivity in methods of evaluating functionality of antibody immune responses. The MIMIC® system is based on cultures of human immune-competent cells developed in a 96-well format, which limits the achievable concentrations and total quantities of the antigen-specific antibodies generated in the system.

Thus, there is a continuing need for functional assays with improved sensitivity, including those based on hemagglutination.

BRIEF SUMMARY OF THE INVENTION

Hemagglutination (HA) and hemagglutination inhibition (HAI) functional assays remain important instruments of analysis of virus-cell interaction and protective efficacy of virus-specific antibodies and sera. However, the classical protocols of HA and HAI demonstrate limited sensitivity towards some viruses and require significant volumes of viruses and the tested sera or antibodies, which can constitute an obstacle when experimenting with scarce or precious materials. The latter is especially important when analyzing the samples obtained from the in vitro systems that model immune responses, such as, for example, the MIMIC® system.

Embodiments of the present invention include a new method for the functional characterization of viruses and virus-specific antibodies and sera, the Surface-Assisted Hemagglutination/Hemagglutination Inhibition functional assay, "SA-HA/HAI." Embodiments of the present invention demonstrate sensitivity of the SA-HA assays to various influenza viruses 7-200 times higher than the traditional HA assay, and sensitivity of the SA-HAI assay to influenza-specific antibodies 7-50 times higher than in the traditional HAI, depending on the types of viruses and erythrocytes used.

Additionally, a version of the SA-HAI assay that uses U-bottom ELISA plates makes it possible to determine the relative contributions of low affinity and high affinity functional antibodies in the HAI titer, which is technically impossible using classical HAI.

There are three major concepts in the foundation of the current invention embodiments:
1) Transferring of the hemagglutination reaction from solution to the activated surface of specially coated (opsonized) plates, or (alternatively) ELISA plates.
2) Using photo-registration of the agglutination micropatterns, digital image processing, calculation of a numerical Hemagglutination Parameter that reflects the degree of agglutination in every well of the plate and the mathematical computation of the titers.
3) Using advanced standardization of the HAI assay that effectively reduces variability in the HAI data.

The enhancement in sensitivity allows analysis of experimental samples of low concentrations and saves precious materials, such as convalescent sera and viruses. The SA-HA/HAI assays can use the same types of erythrocytes as normally used in the traditional HA/HAI assays: human, mammalian, and avian.

Characterizing the relative contributions of low- and high-affinity virus-specific and functional (potentially protective) antibodies in the HAI titer makes the ELISA plate version of the SA-HAI assay a valuable tool that provides deeper insight in the properties of humoral immune responses.

The SA-HA/HAI assay results can be evaluated visually, in the manner similar to the classical HA/HAI assays. However, visual evaluation lacks the precision necessary in high-sensitivity experiments and it is obviously prone to human errors, due to differences in perceptions by different operators. Photo-registration and digital processing of the SA-HA/HAI images increases the precision of the method and eliminates such subjectivity. The image processing can be performed in line with photo registration and in real time. The SA-HA/HAI method can be performed in a high-throughput mode and allows automation.

In a first specific embodiment, the present invention is directed a SA-HA assay. In particular, the method can be used to determine whether virus is present in a sample, as well as to quantify the amount of virus in the sample. In one aspect, the method comprises: (a) incubating a target object and a sample suspected of containing a virus in an opsonized well of a culture plate under conditions permitting agglutination of the target object by the virus, and (b) detecting agglutination of the target object on the surface of the well bottom of (a), thereby determining presence of virus in a sample.

In a second, related embodiment, the present invention is again directed to a SA-HA assay. This method can also be used to determine whether virus is present in a sample, as well as to quantify the amount of virus in the sample. In one aspect, the method comprises: (a) incubating a sample suspected of containing a virus in an activated well of a culture plate, (b) adding a target object to the well of (a) under conditions permitting agglutination of the target object by the virus, and (c) detecting agglutination of the target object on the surface of the well bottom of (b), thereby determining presence of virus in a sample.

In another aspect, the second embodiment further comprises adding a blocking agent to the well of (a), prior to adding the target object. While the skilled artisan will readily recognize suitable blocking agents that may be used in the method, 2% BSA in PBS is a suitable blocking agent.

In each of these embodiments, the virus is a DNA virus, an RNA virus, or a retrovirus. Further, the target object is cells or microspheres. Examples of suitable microspheres include latex microspheres and other microspheres that can be readily bound by virus and agglutinated. In one aspect, the microspheres are latex microspheres coated with a receptor that binds with the virus. Examples of suitable cells include erythrocytes, lymphocytes, epithelial cells, and endothelial cells. In one aspect, the erythrocytes are avian erythrocytes or mammalian erythrocytes, such as human erythrocytes. The cells may be human group O erythrocytes. The cells may also be erythrocytes present at a concentration of below 0.1% hematocrit. In another aspect, the lymphocytes are avian lymphocytes or mammalian lymphocytes, such as human lymphocytes.

In the noted first specific embodiment, the well is opsonized by coating the well with a protein or a lectin. In one aspect, the protein is bovine serum albumin or human serum albumin.

In the noted second embodiment, the plate comprising an activated well is an ELISA plate. In one aspect, the ELISA plate has U-shaped wells. In another aspect, the ELISA plate has V-shaped wells.

In each of the first and second embodiments, the assays may be performed such that the results of the noted methods simply indicate whether virus is present in the sample or not. The presence of a halo form of agglutination indicates the presence of virus, while the presence of a pellet form of agglutination indicates the absence of the virus. However, both embodiments may include further steps of quantifying the amount of agglutination detected. Such information can be directly correlated with the amount of virus in the sample, where the amount of the target object is held constant. A specific determination of the amount of virus in the sample can further be made by comparing the quantified amount of agglutination to a range of quantified agglutination values previously determined for known amounts of the virus in samples, where the amount of the target object is held constant. The amount of agglutination detected can be quantified by quantifying two-dimensional agglutination patterns created by the agglutinated target objects on the surface of the well bottom of the plate. Such quantifying can be performed visually or it can be performed using digital photo registration and digital image processing. The digital image processing can include calculation of a numerical agglutination parameter that reflects the degree of agglutination. The agglutination parameter is a ratio of the size of the image area containing the two-dimensional agglutination patterns on the surface of the well bottom and the average pixel intensity of the agglutination patterns in the area.

In preferred aspects, the agglutination is detected in the first and second embodiments at a sensitivity increased by at least about 10 times compared to performing the methods in a non-opsonized or non-activated well under conditions that provide agglutination in the well volume rather than on the surface of the well bottom.

In a third specific embodiment, the present invention is directed to a SA-HAI assay. In particular, the method can be used to determine whether virus is present in a sample, to quantify the amount of virus in the sample, and to determine functional binding activity of a particular antibody. In particular aspect, the method can be used to determining functional binding activity of a particular antibody and it comprises: (a) incubating an agglutinating factor with an antibody in an opsonized well of a culture plate, (b) adding a target object to the well of (a) under conditions permitting agglutination of the target object by the agglutinating factor, and (c) detecting agglutination of the target object on the surface of the well bottom of (b), wherein when agglutination detected in (c) is less than agglutination detected in the absence of the antibody, the antibody is determined to have functional binding activity.

In a fourth, related embodiment, the present invention is again directed to a SA-HAI assay. In particular, the method can be used to determine whether virus is present in a sample, to quantify the amount of virus in the sample, and to determine functional binding activity of a particular antibody. In particular aspect, the method can be used to determining functional binding activity of a particular antibody and it comprises: (a) incubating an agglutinating factor in an activated well of a culture plate, (b) adding an antibody to the well of (a), (c) adding a target object to the well of (b) under conditions permitting agglutination of the target object by the agglutinating factor, and (d) detecting agglutination of the target object on the surface of the well bottom of (c), wherein when agglutination detected in (d) is less than agglutination detected in the absence of the antibody, the antibody is determined to have functional binding activity.

In another aspect, the fourth embodiment further comprises washing the well of the plate of (c) with a buffered wash solution after adding the antibody to the well. While the skilled artisan will readily recognize suitable wash solutions that may be used in the method, 0.25% BSA+0.25% OVA in PBS is a suitable wash solution.

In another aspect, the fourth embodiment may also further comprise adding a blocking agent to the well of (a), prior to adding the antibody. While the skilled artisan will readily recognize suitable blocking agents that may be used in the method, 2% BSA in PBS is a suitable blocking agent.

In each of these embodiments, the agglutinating factor is a factor selected from the group consisting of a virus, a virus-like particle, a bacterium, and a protein. In one aspect, the agglutinating factor is a virus. Suitable viruses include DNA viruses, RNA viruses, and retroviruses. Further, the target object is cells or microspheres. Examples of suitable microspheres include latex microspheres and other microspheres that can be readily bound by virus and agglutinated. In one aspect, the microspheres are latex microspheres coated with a receptor that binds with the virus. Examples of suitable cells include erythrocytes, lymphocytes, epithelial cells, and endothelial cells. In one aspect, the erythrocytes are avian erythrocytes or mammalian erythrocytes, such as human erythrocytes. The cells may be human group O erythrocytes. The cells may also be erythrocytes present at a concentration of below 0.1% hematocrit. In another aspect, the lymphocytes are avian lymphocytes or mammalian lymphocytes, such as human lymphocytes.

In each of these embodiments, the antibody used in the method may be any antibody that has the potential to agglutinize the target objects. The antibody may be used in the methods as serum comprising the antibody. In one aspect, the serum is a human serum. In another aspect, the serum is an animal serum. In a further aspect, the antibody may be used in the methods as an experimental fluid comprising the antibody, such as MIMIC® supernatant.

In the noted first specific embodiment, the well is opsonized by coating the well with a protein or a lectin. In one aspect, the protein is bovine serum albumin or human serum albumin.

In the noted second embodiment, the plate comprising an activated well is an ELISA plate. In one aspect, the ELISA plate has U-shaped wells. In another aspect, the ELISA plate has V-shaped wells.

In each of the third and fourth embodiments, the presence of a halo form of agglutination indicates the antibody has binding activity, while the presence of a pellet form of agglutination indicates the antibody does not have binding activity. Thus, the methods of these embodiments can provide a simple "yes/no" answer to the question of whether the antibody has binding activity. However, both embodiments may include further steps of quantifying the amount of agglutination detected. Such information can be directly correlated with the binding affinity of the antibody for the target object in the sample, such as a virus. Agglutination may be measured by quantifying two-dimensional agglutination patterns created by the agglutinated target objects on the surface of the well bottom of the plate. Such quantifying can be performed visually or it can be performed using digital photo registration and digital image processing. The digital image processing can include calculation of a numerical agglutination parameter that reflects the degree of agglutination. The agglutination parameter is a ratio of the size of the image area containing the two-dimensional agglutination patterns on the surface of the well bottom and the average pixel intensity of the agglutination patterns in the area. The methods of the third and fourth embodiments can further comprise determining a relative contribution of high affinity antibodies to the agglutination detected in (d) by comparing the value detected in (d) to a value detected in (d) where the well was not washed with a buffered wash solution after adding the antibody to the well.

In preferred aspects, the agglutination is detected in the third and fourth embodiments at a sensitivity increased by at least about 10 times compared to performing the methods in a non-opsonized or non-activated well under conditions that provide agglutination in the well volume rather than on the surface of the well bottom.

BRIEF DESCRIPTION OF THE FIGURES AND TABLES

Figure 1:
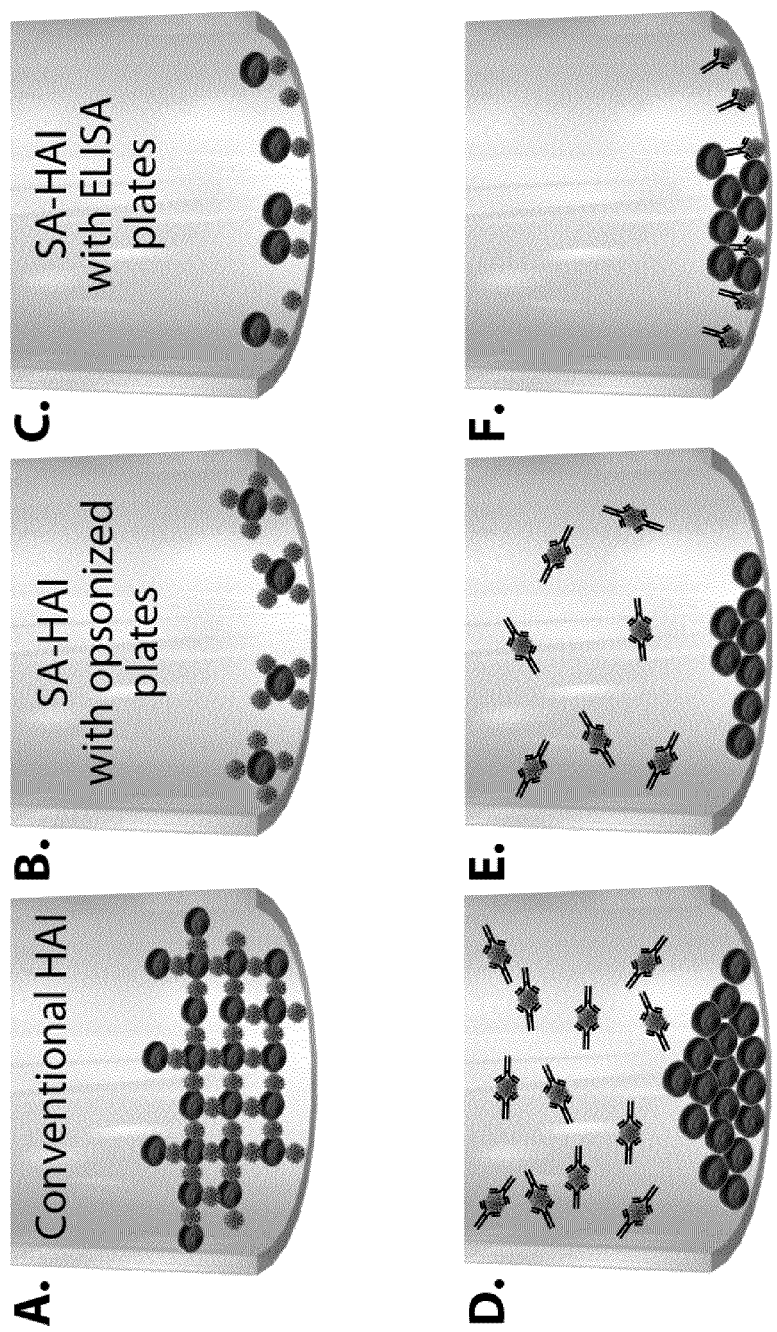

FIG. 1. Patterns of erythrocytes in classical HA/HAI and surface-assisted HA/HAI experiments. Left column: Classical HA/HAI. Central column: Surface-assisted HA/HAI with polypropylene plates soaked with opsonizing solutions. Right column: Surface-assisted HA/HAI with U-bottom ELISA plates pre-coated with the virus. A.—Erythrocytes develop a 3D "lattice" with unblocked viruses (formation of a "halo"). B.—Erythrocytes anchor to the activated walls of the U-shaped well via unblocked viruses (formation of a "micro-halo"). C.—Erythrocytes anchor to the unblocked viruses pre-attached to the walls of the U-shaped well (formation of a "micro-halo"). D.—Erythrocytes sediment to the center of the U-shaped well, unobstructed by viruses blocked with Abs (formation of a "button"). E.—Erythrocytes sediment to the center of the well, unobstructed by viruses blocked with Abs (formation of a "micro-button"). F.—Erythrocytes sediment to the center of the well unobstructed by viruses blocked with Abs (formation of a "micro-button").

Figure 2A:
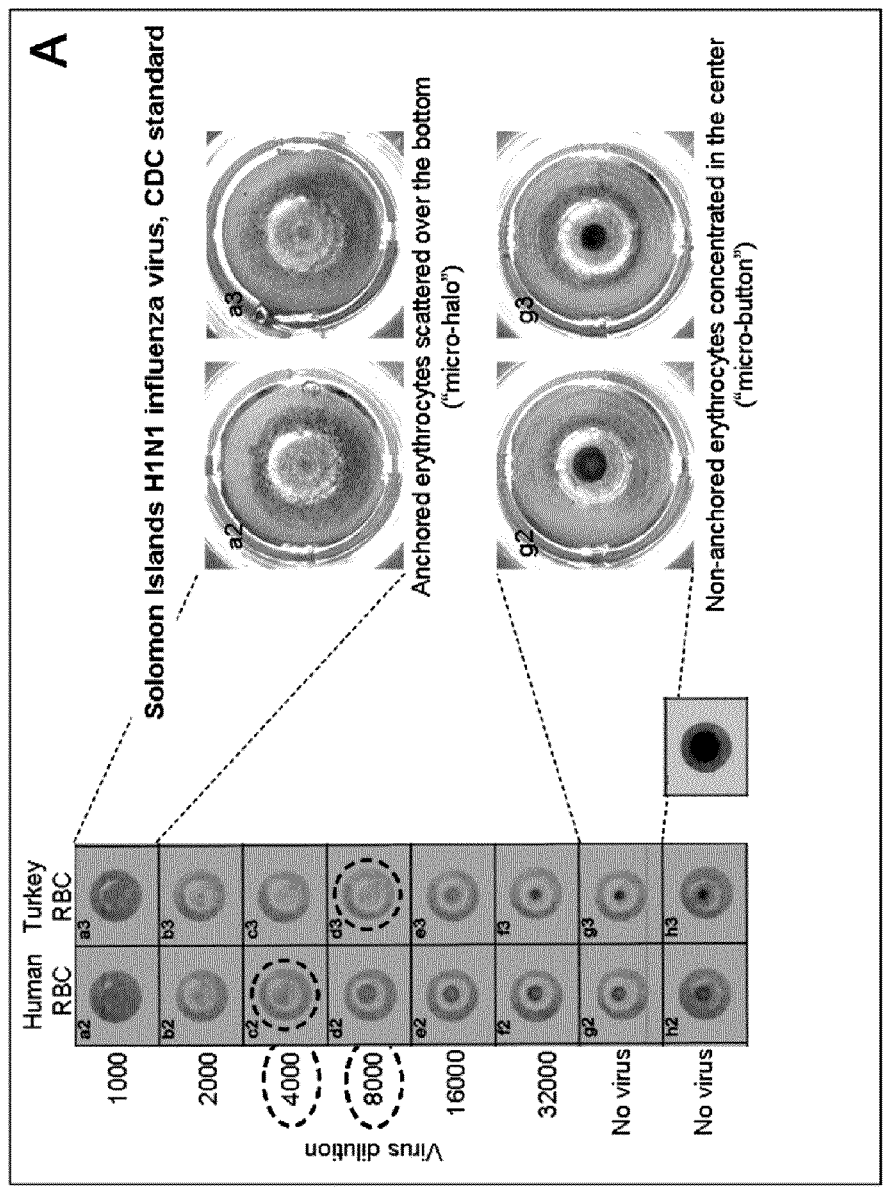
Figure 2B:
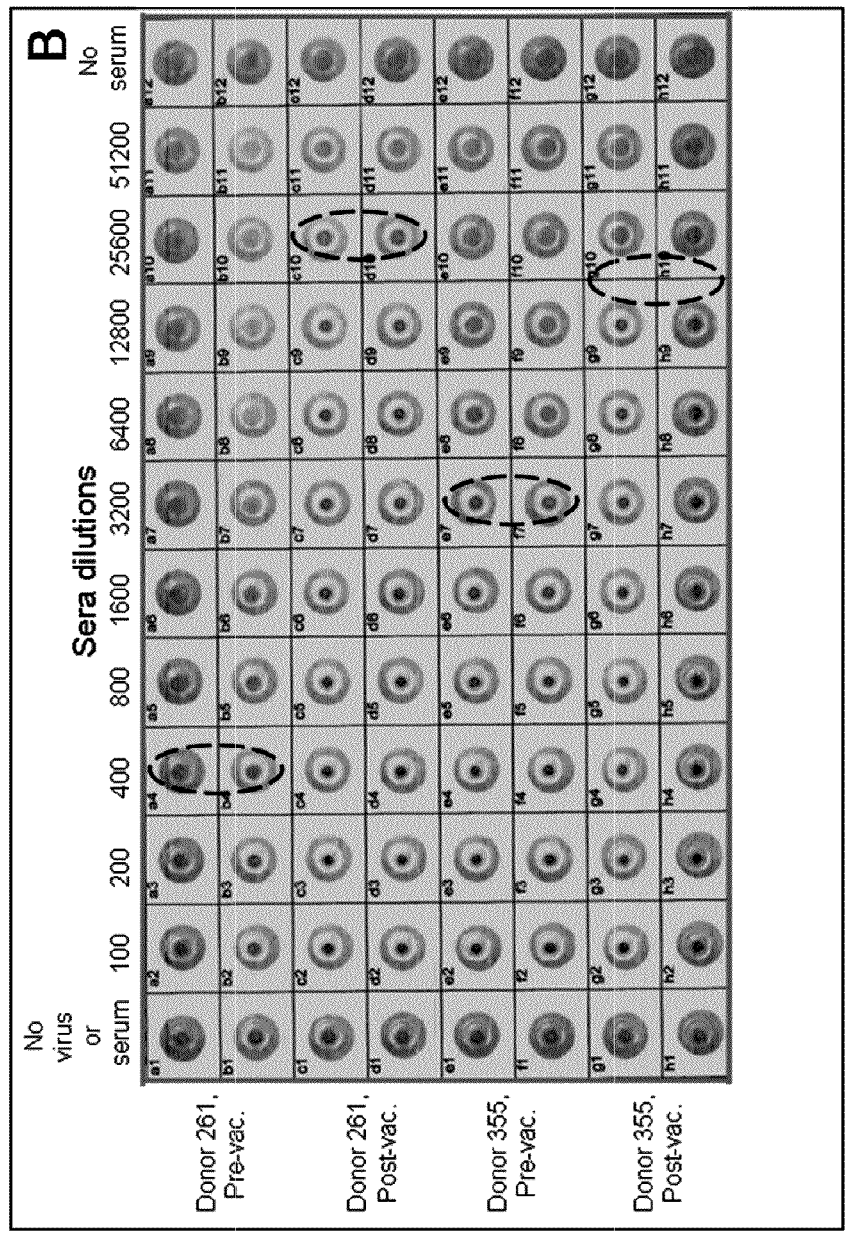

FIGS. 2A-B. Images of surface-assisted HA/HAI experiment with opsonized plates. A. SA-HA experiment with human group O erythrocytes and turkey erythrocytes. Images of the wells with micro-halos and micro-buttons were enlarged from the panel photo-registered in the AID ELISPOT reader (AID ELR04 AID GmbH, Germany). The two vertical columns of wells on the left of the figure show the formation of micro-halos and micro-button at different virus dilutions. Circled are dilutions selected for inhibition assays. The single well shown in the bottom center of the figure is a "button" from a classical HAI for comparison. The magnified images of the four wells to the right were registered using AID ELISPOT reader (Cell Technology Inc., MD). B. SA-HAI experiment with human group O erythrocytes, Solomon Islands H1N1 influenza virus, and sera from the donors immunized for influenza in season 2007/2008. SA-HAI titers were determined visually. Circled are dilutions selected as SA_HAI titers. Circling between boxes designates selection of the intermediate dilution.

FIG. 3. Algorithm of digital processing of hemagglutination patterns. A. General scheme of the algorithm. B. Transformation of the hemagglutination images during image processing.

FIG. 4. Flowcharts for digital processing of SA-HA/HAI plates. A. Selection of the image processing variables, single-well mode. B. General processing algorithm for a single image. C. Single plate processing mode. D. Multiples plate processing mode. E. Plate layout and curve fit data analysis.

FIGS. 5A-C. Typical SA-HAI plate layout. A. Primary image of a typical plate (a real plate presented). Sera samples S108, S111-S114 were placed in duplicates in the columns (vertical layout). Columns 11 and 12 contain a standard serum (shown is serum #10 from a donor immunized for influenza in the 2009/2010 season). B. Processed image of the same plate. Squared with red dash line are the wells containing the standard at the dilution 1:3200, selected as the Standard Linked Dilution (LSD). C. HAP values determined for the same plate. Squared with red dash line are Linked HAP values (LHAP).

FIGS. 6A-B. Using Linked Hemagglutination Parameter in calculation of SA-HAI titer. A. Correcting of the LHAP value in the process of splining of the titration curve. The corrected LHAP is 318. B. Determination of the SA-HAI titer for the sample S112 (i.e., finding the dilution factor corresponding to the spline-corrected LHAP value). The titer is 5045. Shown is an illustrative procedure, performed manually in Excel editor.

FIG. 7. Determination of the SA-HA titer of influenza H1N1 virus. Virus: A/Solomon Islands/3/2006 [H1N1]. Erythrocytes: Turkey. SA-HAI mode: Opsonized plates. Shown is an illustrative procedure performed manually in Excel editor. The SA-HAI titer was found to be ~10090. The classical HA titer was found to be =240 (data not shown).

FIG. 8. Comparison of Full Volume and Low Volume modes of classical HAI assay. Virus: A/Brisbane/59/2007 [H1N1], BPL-inactivated CDC standard. Erythrocytes: Turkey. Full Volume Mode Component aliquots 30 μL, final volume 90 μL, U-bottom polystyrene 96-well plate (image made with a digital camera). Low Volume Mode: Component aliquots 7 μL, final volume 21 μL, V-bottom polypropylene 96-well plate (image made with an ELISPOT plate reader).

FIGS. 9A-B. A.—Comparing classical HAI and SA-HAI titers for donor sera using human erythrocytes and Solomon Islands H1N1 virus. SA-HAI assays were performed using opsonized plates. Donor pre- and post-vaccination sera: From 15 donors immunized for influenza in the season 2007/2008. Erythrocytes: Human group O. Virus: A/Solomon Islands/3/2006 [H1N1], BPL-inactivated standard from the US Centers for Disease Control and Prevention, Atlanta, Ga. B.—Dataset used in A.

FIGS. 10A-B. A.—Comparing classical HAI titers determined with human erythrocytes and SA-HAI titers with turkey erythrocytes. Experiments were performed with pre- and post-vaccination sera from 15 donors immunized for influenza in the season 2007/2008. SA-HAI assays were performed using opsonized plates. Erythrocytes: classical HAI—human group O; SA-HAI—turkey. Virus: A/Solomon Islands/3/2006 [H1N1], BPL-inactivated standard from CDC. B.—Dataset used in A.

FIG. 11. Comparing classical HAI titers determined with human erythrocytes and SA-HAI titers using guinea pig erythrocytes. SA-HAI assays were performed using opsonized plates. The experiment was performed with pre- and post-vaccination sera from three donors immunized for influenza in the season 2007/2008. Erythrocytes: classical HAI—human group 0; SA-HAI—guinea pig. Virus: A/Solomon Islands/3/2006 [H1N1], BPL-inactivated standard from CDC.

Figure 12A:
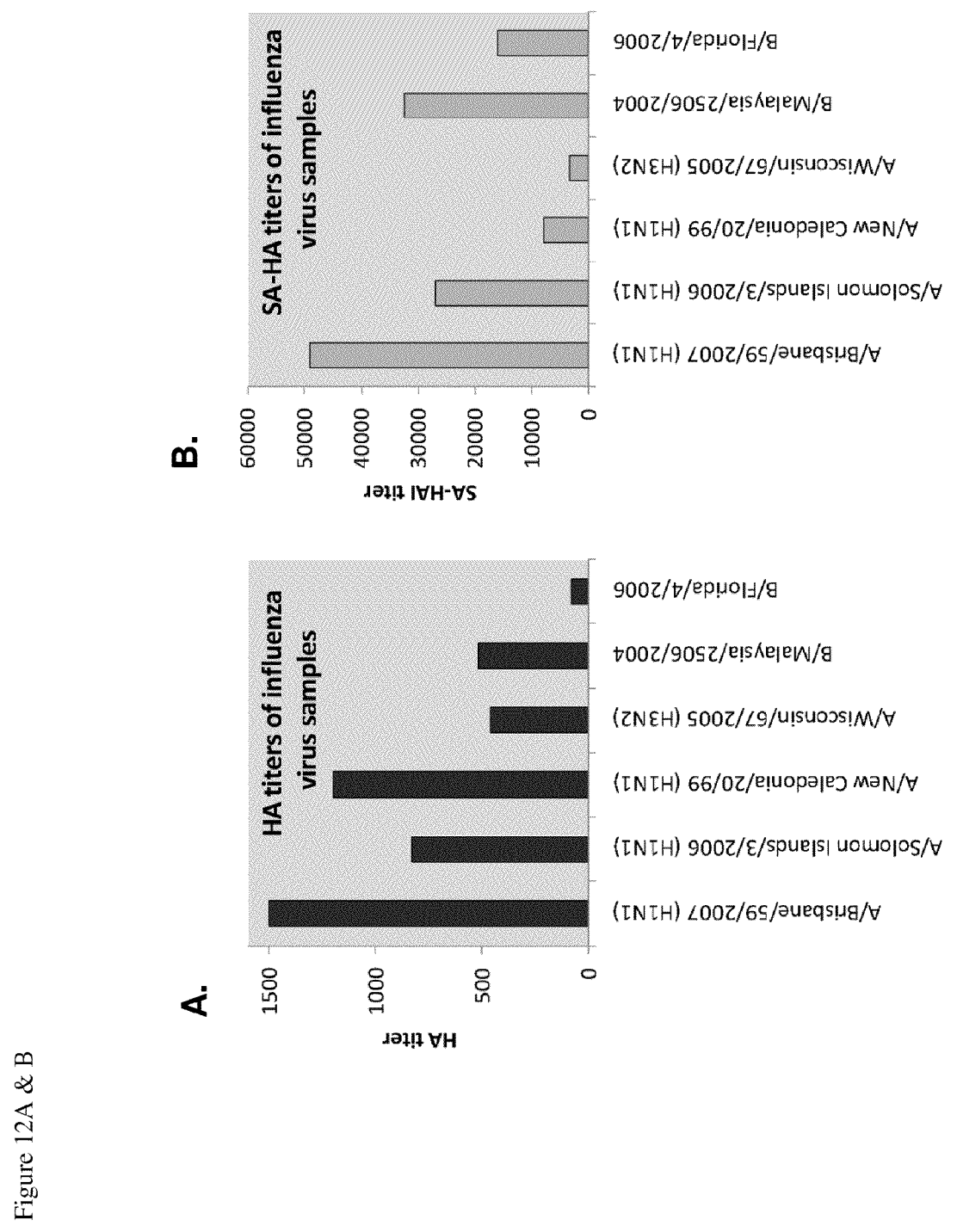

FIGS. 12A-C. Comparing classical HA titers (A.) and SA-HA titers (B.) for influenza viruses in allantoic fluids. SA-HA assays were performed using ELISA plates Immulux HB immunoassay microplates (Dynex Technologies, catalog #1011). Classical HA assays were performed in Low Volume mode using V-bottom polypropylene plates. Erythrocytes: Turkey. Viruses: Mice allantoic fluids, year 2010. C.—Datasets used in A. and B.

FIG. 13. Comparing classical HAI and SA-HAI titers using turkey erythrocytes and H1N1 influenza virus in allantoic fluids. Virus: A/Brisbane/59/2007 [H1N1]. Other experimental conditions: As in FIG. 12.

FIG. 14. Comparing classical HAI and SA-HAI titers using turkey erythrocytes and H3N2 influenza virus in allantoic fluids. Virus: A/Wisconsin/67/2005 [H3N2]. Other experimental conditions: As in FIGS. 12 and 13.

FIGS. 15A-B. SA-HAI analysis of cross-protection against swine flu with seasonal influenza vaccine 2009/2010. SA-HAI assays were performed using opsonized plates. Sera: From 27 donors immunized with the anti-influenza Fluvirin vaccine in season 2009/2010, pre- and post-vaccinated. Viruses: A/Brisbane/59/2007 [H1N1] (A.) and A/California/7/2009 [H1N1](B.), BPL-inactivated standards from CDC. Erythrocytes: Turkey. Protective SA-HAI level ~640 was derived as a product of the protective titer accepted in the classical HAI (−64) and the factor of sensitivity enhancement in the SA-HAI assays (~10-fold).

Figure 16:
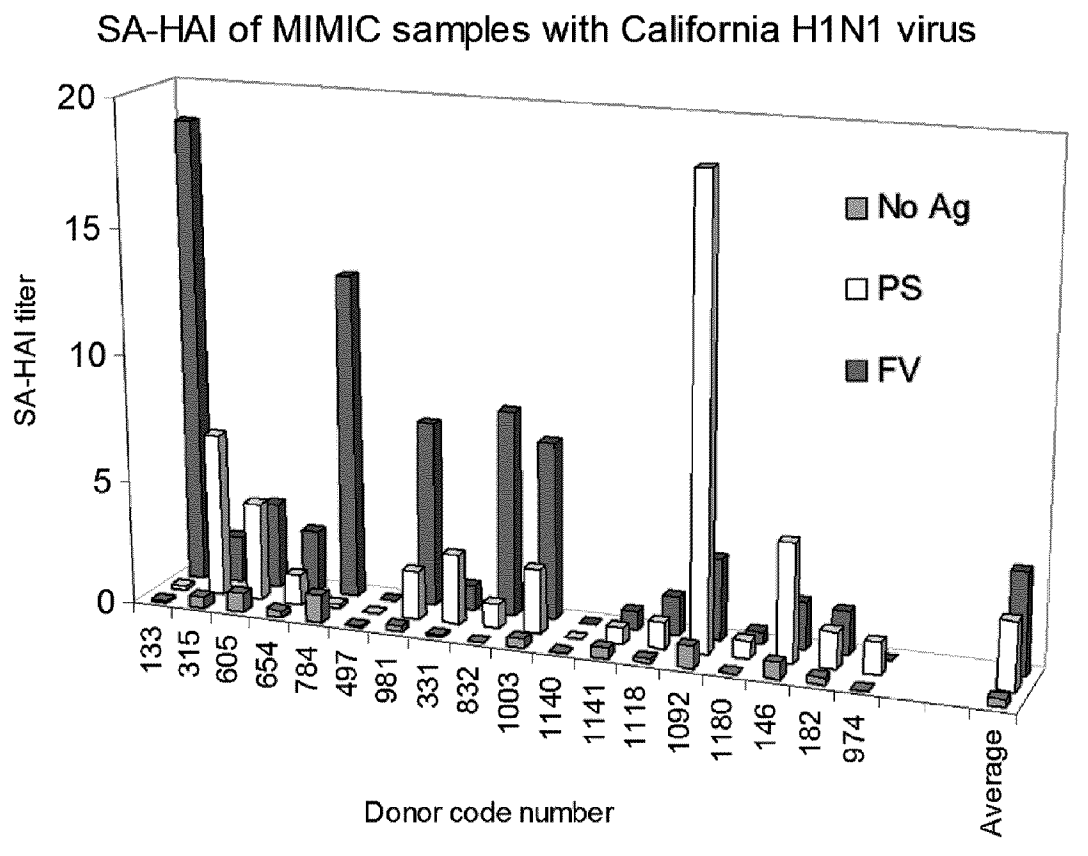

FIG. 16. SA-HAI analysis of samples from in vitro MIMIC® setups immunized with vaccine and recombinant antigen. SA-HA assays were performed using ELISA plates Immulux HB immunoassay microplates (Dynex Technologies, catalog #1011). MIMIC® setups based on immune cells from human donors were immunized in vitro with the Fluvirin-2010 seasonal vaccine and with recombinant H1 hemagglutinin that originated from the A/California/7/2009 [H1N1] "Swine Flu" virus (Protein Sciences). Erythrocytes: Turkey. Virus in the SA-HAI assay: A/California/7/2009 [H1N1], BPL-inactivated standards from CDC.

FIG. 17. Testing affinity profile of potentially protective antibodies in human sera (A.) and MIMIC® samples (B.) with SA-HAI assay. Human sera: From donors immunized with Fluvirin in season 2009/2010. MIMIC® sample: From MIMIC® setup made using immune cells from donor #654, year 2010. PS antigens: Recombinant H1 hemagglutinin derived from A/California/7/2009 [H1N1] "Swine Flu" virus (Protein Sciences).

DETAILED DESCRIPTION OF THE INVENTION

As used herein, the term "antibody" is used in the broadest sense and encompasses monoclonal antibodies, polyclonal antibodies, chimeric antibodies, humanized antibodies, single-chained antibodies, and antibody fragments (e.g., Fab, F(ab'), Fv) from various mammalian and avian species. Antibodies useful in the methods of the invention have the shared characteristic of a potential for having functional binding activity for an agglutinating factor, such as a virus, or a target object, such as an erythrocyte. Thus, the antibodies have the potential for binding and causing agglutination. Reference to a "potential" simply means that the antibodies are of a type known to have such a characteristic. It will not be known until after the antibodies are assayed whether they do, in fact, have functional binding activity for an agglutinating factor or a target object, or whether they can bind and cause agglutination.

As used herein, an "agglutinating factor" is a molecule that has the potential to agglutinate the target objects of the present invention. Agglutinating factors include viruses, virus-like particles, bacteria, proteins. Suitable viruses include DNA viruses, RNA viruses, and retroviruses. Specific viruses include adenoviruses, enteroviruses, reoviruses, myxoviruses (including the influenza viruses), poxviruses, and flaviviruses.

As discussed above, viruses may be detected and/or quantitated using the methods of the present invention. Viruses that may be detected and/or quantitated using the methods include any virus that have the potential to form an agglutination with target objects, such as erythrocytes. Suitable viruses include DNA viruses, RNA viruses, and retroviruses. Specific viruses include adenoviruses, enteroviruses, reoviruses, myxoviruses (including the influenza viruses), poxviruses, and flaviviruses.

The target objects used in the methods of the invention are those that can agglutinate upon binding with the agglutinating factors of the present invention. The particular identity of the target object is not critical, as long as the characteristics of the object permit consistent, reproducible results in the methods of the present invention. Suitable target objects include cells and microspheres. The cells may be a population of one particular cell type, such as erythrocytes, lymphocytes, epithelial cells, and endothelial cells. An exemplary population is a population of erythrocytes. The source of the erythrocytes is not particular important, as long as the cells have the potential to form an agglutination in the presence of an agglutinating factor such as a virus. Suitable erythrocytes include avian erythrocytes, such as chicken erythrocytes and turkey erythrocytes, and mammalian erythrocytes, such as human erythrocytes, guinea pig erythrocytes, mouse erythrocytes, rat erythrocytes, bovine erythrocytes, equine erythrocytes, goat erythrocytes and sheep erythrocytes. Human erythrocytes may be from a donor of any blood group, such as group A erythrocytes, group B erythrocytes, group AB erythrocytes, and group O erythrocytes. Examples of suitable microspheres include latex microspheres and other microspheres that can be readily bound by virus and agglutinatized. In one aspect, the microspheres are latex microspheres coated with a receptor that binds with the virus.

In certain aspects, erythrocytes may be used as the target objects, and the concentration of the erythrocytes can be selected such that they are present in a well of a plate at a concentration of below about 0.01% hematocrit, below about 0.05% hematocrit, below about 0.1% hematocrit, below about 0.15% hematocrit, or below about 0.2% hematocrit.

As discussed above, the methods of the present invention may be practiced using culture plates, such as tissue culture plates, where the wells have been opsonized by coating the well with a protein or a lectin. The wells may be opsonized by inserting a solution comprising one or more proteins, and/or one or more lectins into the well, and allowing the proteins and/or lectins to attach to the surface of the well. The solution can then be removed from the well, and the well can optionally be washed. Suitable proteins include bovine serum albumin and human serum albumin. Serum albumin from other mammalian species may be used as well, such as from goat, horse, pig, rabbit, mouse and rat. As further discussed above, the methods of the present invention may be practiced using culture plates where the wells are activated. Plates having wells with such a characteristic include plates commercially available for use in ELISA assays. While the shape of the wells used in the methods of the present invention may vary depending on the particular steps being used, plates having U-shaped wells and plates having V-shaped wells are particularly useful.

As used herein, a "sample" refers to any type of material of biological origin including, but not limited to, a cell, fluid, tissue, or organ isolated from a subject, including, for example, blood, plasma, serum, fecal matter, urine, semen, bone marrow, bile, spinal fluid, lymph fluid, samples of the skin, external secretions of the skin, respiratory, intestinal, and genitourinary tracts, tears, saliva, milk, blood cells, organs, or biopsies.

As discussed above, agglutination is detected in the first and second embodiments at a sensitivity higher than that achieved when the methods are performed in non-opsonized or non-activated wells and under conditions that provide agglutination in the well volume rather than on the surface of the well bottom. The sensitivity is increased by at least about 7 times, 8 times, 9 times, 10 times, 20 times, 30 times, 40 times, 50 times, 60 times, 70 times, 80 times, 90 times, 100 times, 150 times, or even 200 times, or more. Similarly, agglutination is detected in the third and fourth embodiments at a sensitivity higher than that achieved when the methods are performed in non-opsonized or non-activated wells. The sensitivity is increased by at least about 7 times, 8 times, 9 times, 10 times, 20 times, 30 times, 40 times, or even 50 times, or more.

Decreasing the Concentrations of Viruses and Erythrocytes to Increase Sensitivity of HA/HAI Assay The concentrations of virus and erythrocytes used in the HA/HAI assay dictate sensitivity of the method. For higher sensitivity, the concentration of the virus used in the assay should be reduced as much as possible. While this statement is self-explanatory for the sensitivity to the virus itself in HA mode, a lower concentration of the virus used in the HAI mode would also result in lower concentrations of antibodies in the experimental fluids necessary for blocking attachment of the virus to the erythrocytes, which is equivalent to increasing sensitivity to the tested sera and antibody solutions.

However, reducing the virus concentration in the classical HA/HAI assays is limited by need to discriminate between agglutination and non-agglutination of the erythrocytes by the virus. Specifically, in HA assays the titer determined for the virus is equal to the virus dilution showing the borderline between agglutination and non-agglutination. In fact, the HA titer manifests the virus concentration below which no functional observation is possible within the given assay. This is why the concentration of the virus in the HAI assay is normally maintained four times higher than the virus titer (Hierholzer et al. (1969) *Applied Microbiol.* 18, 824-833; WHO Manual on Animal Influenza Diagnosis and Surveillance, WHO/CDS/CSR/NCS2002.5 Rev. 1).

In classical HA/HAI, the agglutination/non-agglutination discriminating signal is the formation of a halo of the erythrocytes glued into the spatial lattice by virus particles, or a button of precipitated erythrocytes.

It would seem that the virus concentration could be lowered further if the corresponding concentration of the erythrocytes could be decreased as well. This pathway, however, is also limited within the classical HA/HAI method, because at erythrocyte concentrations below ~0.1-0.2% hematocrit (HCT), formation of the spatial lattice of erythrocytes glued by virus particles becomes impossible.

Thus, to overcome physical limitations of the classical HA/HAI assay, development of new alternative methods was necessary.

Principles of the Surface-Assisted HA/HAI Method

The method was developed in two versions, considered separately below.

Surface-Assisted HA/HAI Using Opsonized 96-Well Plates

While exploring decreased erythrocyte and virus concentrations in the classical HA/HAI assay, new effects were revealed. Specifically, if U-bottom plates, such as 96-well U-bottom plates, were used and pre-soaked with certain opsonizing solutions, such as solutions of bovine or human serum albumin (BSA, HSA), then the erythrocytes bearing influenza viruses attached to their surfaces anchored to the opsonized surface of the well upon precipitation and stayed attached, forming a two-dimensional "micro-halo," as opposed to the three-dimensional halo in the classical HA/HAI (FIG. 1; central and left panels). When the virus was absent or blocked with virus-specific antibody, the precipitating erythrocytes were not able to anchor to the opsonized surface and gradually concentrated near the center of the well bottom, due to Brownian motion, thus forming a "micro-button." Importantly, these effects were observed at concentrations of erythrocytes 20-50 times lower, and influenza viruses 30-600 times lower than in the classical HAI, depending on the virus strains.

Characteristic patterns of the Surface-Assisted HA/HAI (SA-HA/HAI) using opsonized plates are presented in FIG. 2. In all examples of SA-HA/HAI experiments with opsonized plates presented in the current application, opsonization was performed with high-grade BSA solution, 2% in PBS/NaN$_3$ saline. Other opsonizing solutions can be used, for example solutions of glycoproteins, such as lectins.

Surface-Assisted HA/HAI Using ELISA Plates

In another embodiment of the present invention, an alternative version of the SA-HA/HAI was developed based on 96-well ELISA plates (FIG. 1; right columns). Specifically, U-bottom ELISA plates (for example, Immulux HB from Dynex, catalog #1011, or ImmunoGrade plates from BrandTech Scientific, catalog #781724) were first coated with influenza virus and then blocked with 2% high grade BSA in a manner similar to a regular ELISA protocol. Erythrocytes applied to such plates anchored to the virus particles already attached to the ELISA surface, forming a two-dimensional "micro-halo" that looked quite similar to that observed in the experiments with opsonized plates. Application of anti-virus sera or antibodies on the top of the pre-attached viruses abolished the anchoring of erythrocytes to the attached viruses, and precipitating erythrocytes gradually concentrated near the center of the well, forming a "micro-button," similar to that described for the SA-HAI using opsonized plates (FIG. 1; right panel).

Digital Image Processing and Analysis

Results of the SA-HA/HAI experiments can be evaluated visually, in a manner similar to the classical HA/HAI. However, using image processing makes such evaluation more precise and significantly reduces the subjectivity of operator.

HA/HAI Image Acquisition

Digital images of HA/HAI assay wells can be recorded using an automated imaging system capable of taking high-resolution images of individual wells on a 96-well plate. Adequate systems are available commercially, such as those designed for EliSpot assay analysis, that can acquire the digital images necessary for HA/HAI image analysis. For example, images of HA/HAI assay wells can be recorded on an AID ELISPOT plate reader and stored in JPEG format at 1088×1036 resolution and 24-bit color depth are adequate for HA/HAI analysis. The image acquisition software included with these systems is typically full-featured in terms of camera and translation stage control, well selection, and file management; however the included software is intended for ELISPOT analyses and is not capable of proper quantification of HA or HAI titers. Thus, these types of imagers are useful only for their image acquisition capabilities, and the recorded HA/HAI well images were processed using software developed specifically for determining the HA/HAI titers, as described below.

Concept of the Hemagglutination Parameter, HAP

To quantify and compare hemagglutination patterns in different wells, a numeric parameter was devised that was able to characterize the degree of agglutination of the erythrocytes used in the assay. The hemagglutination patterns formed by erythrocytes in the SA-HA/HAI assay can be "buttons," "halos," or intermediate between the two. Two main properties of such patterns are evident: the area over which erythrocytes attach to the well surface and the density of erythrocytes per area unit. These properties were used to calculate a numeric value, called the Hemagglutination Parameter (HAP) which is proportional to the degree of agglutination observed in the given well. The HAP parameter can be defined as $$HAP = <R>/<I> \quad (1),$$

where $<R>$ is the average distance of a pixel from the center of the hemagglutination pattern (HA spot), and $<I>$ is the average intensity of the pixels in the area. The HAP is minimal for the "button" pattern and maximal for the "halo" pattern. The hemagglutination titration curves in the SA-HA or SA-HAI assays can thus be presented as sets of the HAP values linked to the serial dilutions of the virus or sera, respectively, depending on the type of assay. Curve fitting and curve dissecting applied to such a dataset allows precise determination of the titration point. Thus, development and use of the numerical Hemagglutination Parameter transferred the analysis of the HA or HAI assays from subjective visual evaluation to a precise mathematical calculation. The principles of the calculation of the Hemagglutination Parameter (HAP) can be applied to similar calculations of Agglutination Parameters for the target cells other than erythrocytes, or for the target objects other than cells, such as latex beads.

Image Processing Algorithm

The objective of the HA/HAI image processing algorithm is to separate the hemagglutination pattern from the rest of the well image and to then determine the HAP value. The algorithm developed for the SA-HA/HAI assay is illustrated by the flowchart in FIG. 3A. The process is as follows.

Figure 3:
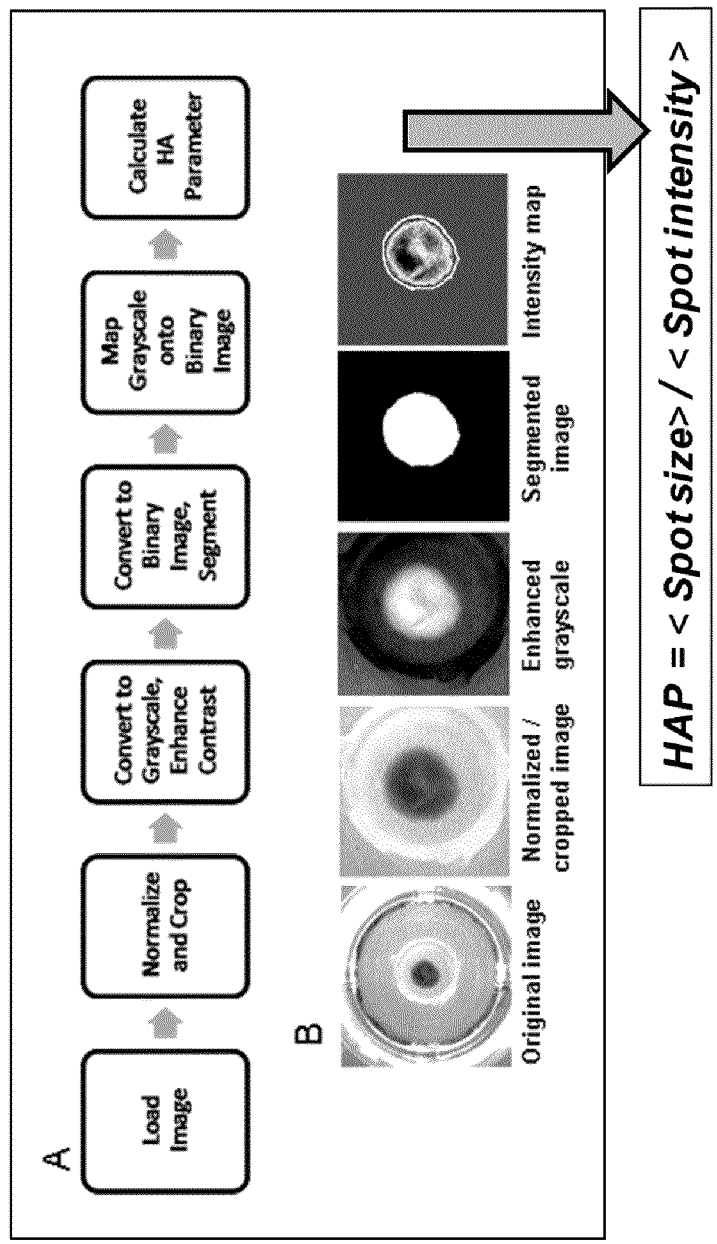

First, an image of the well is obtained as described above. The well image is then cropped to primarily encompass the central pattern-containing portion of the well. The cropped image is converted to negative grayscale and then the contrast is adjusted to fill the entire intensity spectrum and enhance the hemagglutination spot. Intensity thresholding is applied to remove pixels not corresponding to erythrocytes. The image is then segmented using either edge detection or color segmentation algorithms to isolate the erythrocyte pattern. Edge detection, as illustrated in FIG. 3B, required converting of the color image to a binary (black and white) image and segmentation using a binary gradient mask, followed by dilation, hole filling, and image erosion. The resulting segmented binary image represents the HA spot pixels, with all background pixels eliminated. The grayscale image is then mapped onto the segmented binary image, giving an intensity image of the HA spot. The average distance from the spot centroid <R> and average intensity of the spot <I> are calculated from the intensity image, and finally the HAP value is calculated as the ratio (1) above.

Single Well Image Processing Mode (Pre-Processing)

The user has control over some of the analysis variables and must either choose their values prior to image processing or accept default values. These variables include, for example, threshold intensity, crop area, and image segmentation type. Once these values are selected they will be applied to all wells in a batch, be it an entire plate or multiple plates. To optimize the detection of the HA/HAI pattern a priori, the software has a single-well processing mode that allows a user to experiment with the analysis variables on a single well image before applying them to an entire batch. The process is illustrated in the flowchart in FIG. 4A. A user selects the single-well analysis mode, loads a single-well image and then sets the analysis variables. The image is then processed using the algorithm illustrated by flowcharts in FIGS. 3A and 4B, and the resulting HAP value is displayed, as well as the processed image, showing the detected hemagglutination pattern. The user then accepts the values and continues with batch processing or iteratively adjusts the variables and re-processes the image until acceptable values are established. Typically, values are chosen to provide proper detection of the HA/HAI pattern for the two control cases: the No Virus case in which a micro-button is formed in the well bottom and the No Sera case in which a micro-halo is formed. Because these cases represent the hemagglutination extremes, proper detection of their patterns increases the likelihood of proper detection of the hemagglutination patterns for all wells in the batch.

Full Plate Image Processing Mode

Figure 4:
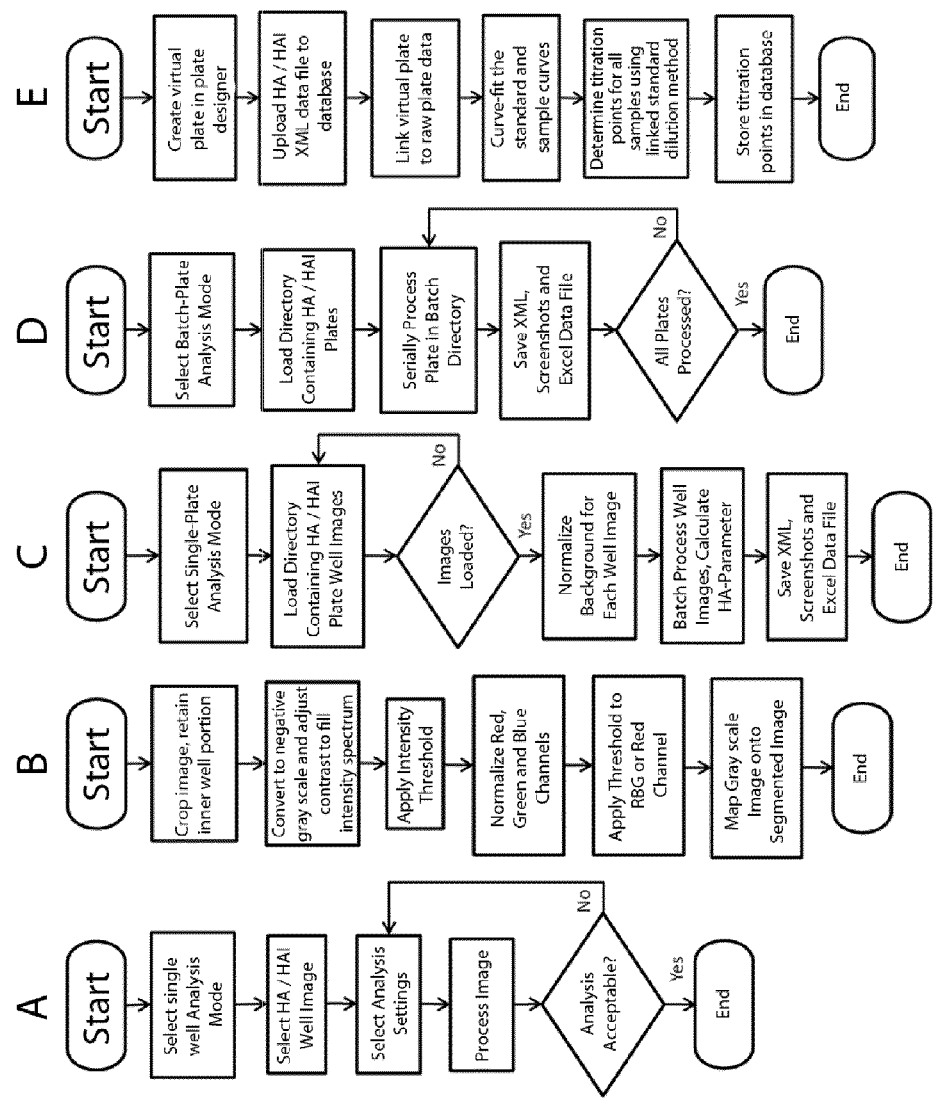

Once pre-processing is complete and acceptable variable values are found, an entire plate can be processed, as illustrated by the flowchart in FIG. 4C. A user selects the single-plate analysis mode and then loads a directory which contains images of wells from the plate. The software verifies that the images are valid for processing and then normalizes the background intensity for all images in the folder by sampling each image around the well periphery and normalizing all wells to the maximum average intensity found. The HA/HAI well images are then batch-processed by applying the algorithm presented in FIG. 4B to each well serially until all wells have been processed. Once a well is processed, its HAP value is readily determined and the results are automatically written to a data file in XML format along with its calculated background value and the analysis variables. Screenshots of the original and processed plate images are also saved along with an Excel file containing the formatted HA parameter values for each well.

Multiple Plate Batch Processing Mode

Multiple-plate batch processing mode allows processing of multiple plates at once using the same settings for each plate. This mode requires minimal user interaction and is intended for high-throughput image analysis. The process is illustrated by the flowchart in FIG. 4D. The user first performs a pre-process analysis to determine proper variable values and then selects batch plate analysis mode. A directory containing multiple plate directories is then selected and each plate directory is processed serially, similar to the full-plate processing mode. The process continues until all plate directories have been processed. If a directory has been processed previously, the software will check for any missing data files, such as screenshots or Excel files and either re-create them if an XML file is present or re-process the plate in its entirety.

Web-Based Curve-Fitting and Data Analysis Application

After a SA-HA/HAI plate is processed, the titration curves need to be curve-fitted to determine their titration points using the Linked Standard Dilution/Linked HAP value method, LSD/LHAP (below). To address high-throughput analysis of the serial assays, a web-based automated curve fitting and database interface application was developed. The application can automatically curve-fit the SA-HA/HAI titration curves using a weighted five-parameter logistic equation, find the titration point using the LSD/LHAP method and then catalog the results into a central database that can be accessed by multiple users simultaneously. The software comprises four main modules: a plate designer module, a file upload module, a curve-fitting module and a database module. As illustrated in FIG. 4E, the user first creates a virtual plate in the plate designer module and defines the HA/HAI plate layout including all reagent and cell information for each well such as name, type, concentration or dilution, and lot or donor number. The virtual HA/HAI plate is stored in the database and can be linked to actual plate data. After a plate is image-processed, the user then uploads the XML file to the database using the file upload module and links the actual data to the corresponding virtual plate. At this point, the plate is well-defined in the database and ready for curve-fitting. The curve-fitting module automatically fits a five-parameter logistic equation to the defined sample and standard curves on the plate and a user-defined linked dilution is applied to find the titration point for each sample on the plate. The titration point is stored in the database and made available to users through the database module, which supports complex queries for data mining, plotting and dataset creation. The database module can export plots or datasets for use in reports or further analysis using other software.

Concept of Linked Standard Dilution and Linked Hemagglutination Parameter, LSD/LHAP The concept described below is another important element of the SA-HAI method, along with transferring the agglutination reaction from the solution to the activated surface, and with digital image processing and computation of the numerical hemagglutination parameter. HA and HAI assays are prone to significant variability, caused by instability of the virus agglutinating capacity, changes in temperature, and variation in the quality of erythrocytes. To increase reproducibility and stability of the SA-HA/HAI data, an advanced standardization protocol named Linked Standard Dilution/ Linked Hemagglutination Parameter (LSD/LHAP) was developed.

Figure 5A:
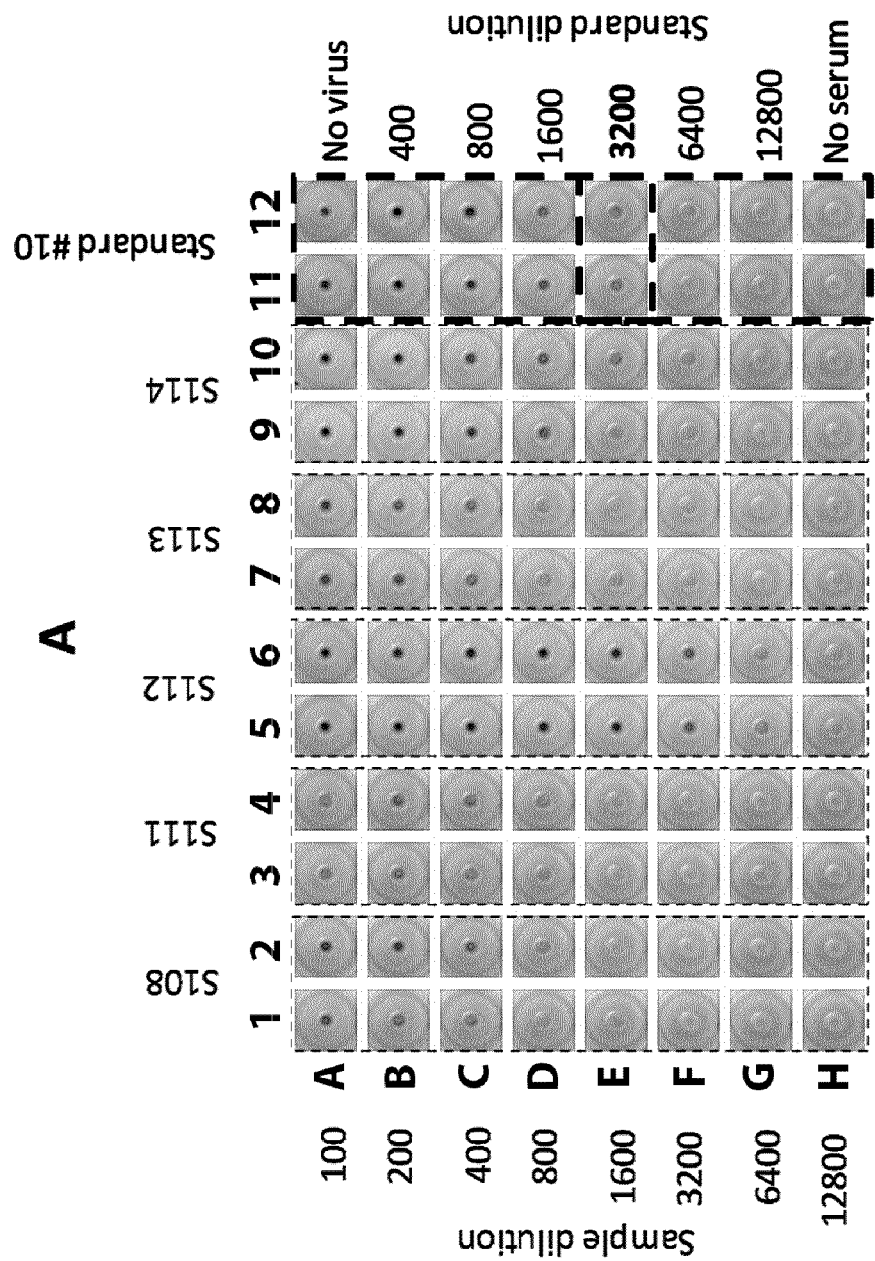
Figure 5B:
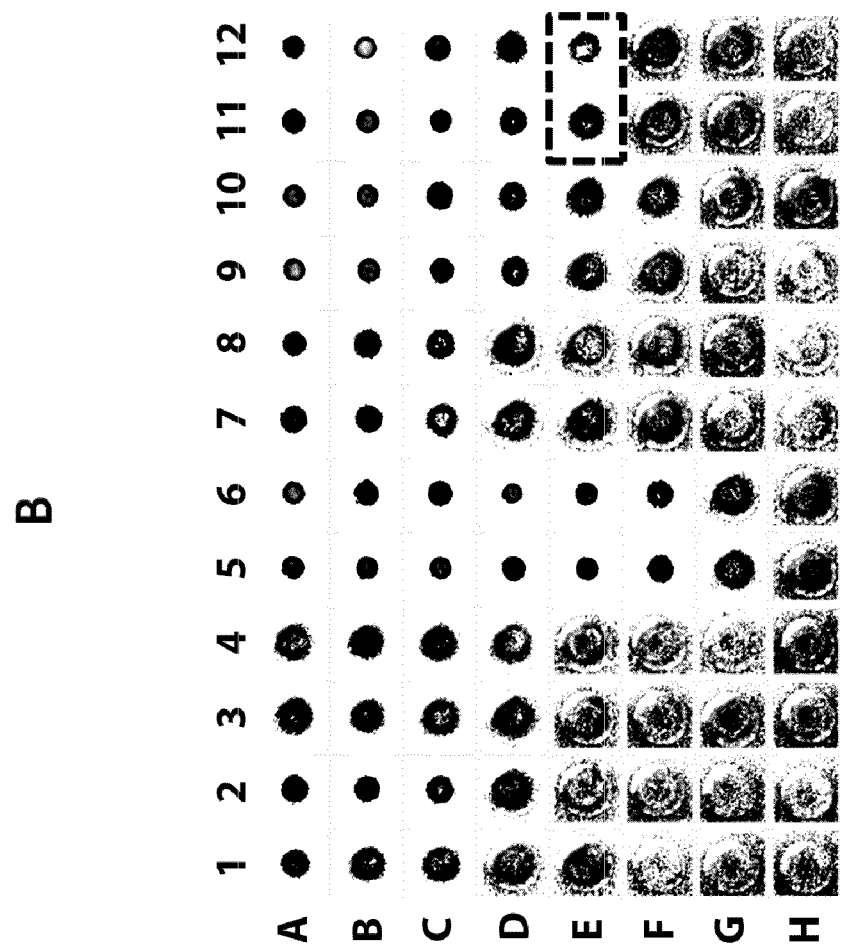

Using the LSD/LHAP approach, every SA-HAI plate is organized in a strictly standardized way (FIG. 5). The samples are serially diluted in the columns 1 to 10 of the 96-well format, in duplicate. Columns 11 and 12 are occupied with a serum selected as a standard for all the SA-HAI plates that are going to be used within a project. Wells A11 and A12 contain no virus and no serum (double negative control), and wells H11 and H12 contain virus but no serum (single negative control). The standard serum is serially diluted six times starting from the wells B11 and B12, down to the wells G11 and G12, in such a manner that wells containing the standard demonstrate the whole dynamic range of the HAI titration, from a clear micro-button to a clear micro-halo. A Linked Standard Dilution (LSD) is selected in the middle of the standard titration array in such a way that the hemagglutination pattern would be between halo and button, as it takes place for wells E11 and E12 containing the standard serum (#10) diluted 1:3200, as shown in FIG. 5.

Figure 6A:
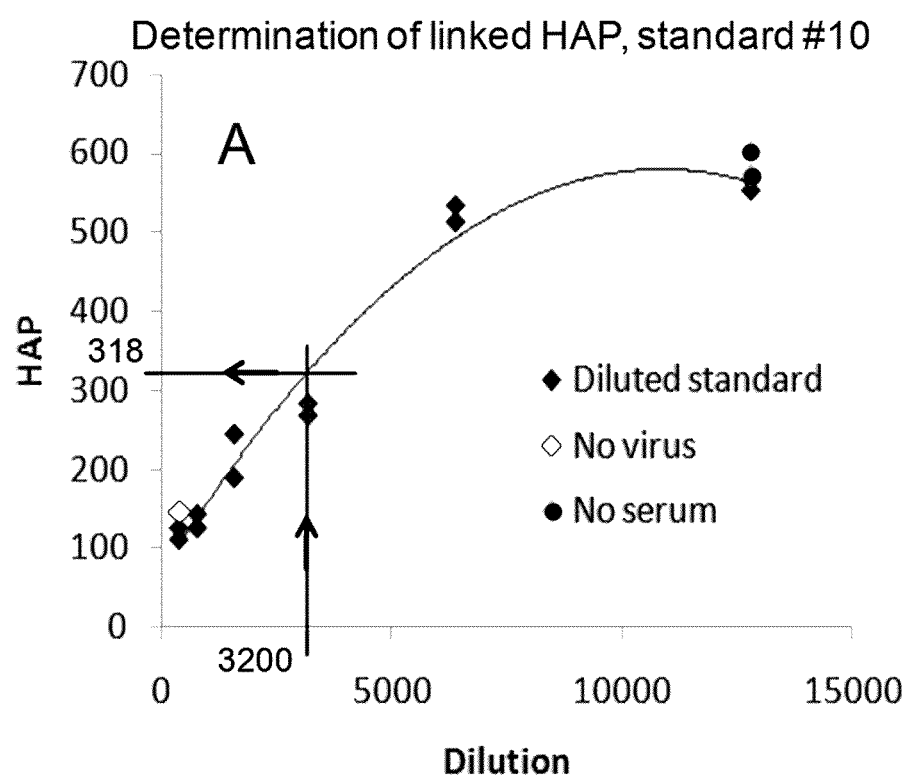
Figure 6B:
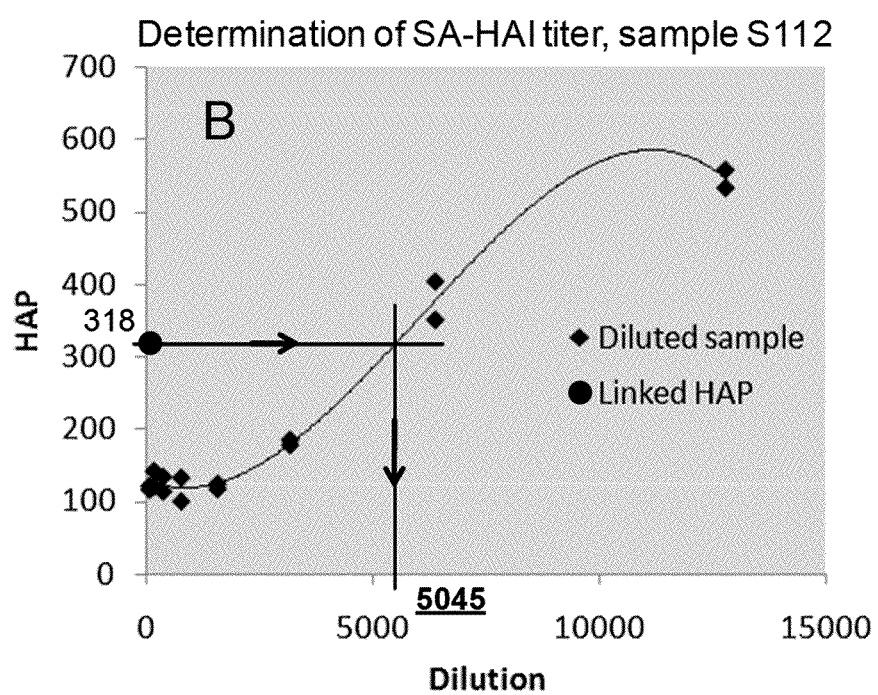

The HAP value that is determined for the chosen LSD is named Linked HAP, or LHAP. The final LHAP value can differ to a certain extent from the numerical values determined for the LSD wells, because the titration curve is set using a splining procedure that smoothes random scattering of the datapoints (FIG. 6A). The LSD parameter is kept the same for all the setups performed in a whole study. The LHAP value found for the standard sera in each plate is used as a titration target for all the tested samples in the plate (FIG. 6B). This means that the final objective for the software that processes the HAI titration curves of the tested sera for a given SA-HAI plate is the calculation of sample dilutions that would provide the HAP values equal to the LHAP value determined for the standard serum in the plate.

If, for example, the room temperature, the quality of erythrocytes, or the virus agglutination capacity, e.g., changes during a long-term study, the hemagglutination patterns in the LSD wells of the standard serum would change accordingly (for example, become closer to a button if the agglutinating capacity decreases), and the corresponding LHAP would change as well (for this example, decreases). However, the corresponding HAP values in the wells with the tested sera will shift in the same direction as the LHAP (for this example, decrease). As a result, because the software uses the changed LHAP as the updated titration target, the resulting SA-HAI titers of the tested sera will remain practically unchanged.

Testing Affinity Profile of Functional Antibodies in SA-HAI Assay with ELISA Plates The classical HAI assay integrates neutralizing effects of functional antibodies having different affinities. Other immunosorptive methods, such as ELISA are able to characterize only antibodies of relatively high affinity. The reason for such difference is that in the classical HAI the complexes of antibodies with the virus do not pass through the procedures of sample removal and washing, which constitutes a backbone of the majority of immunosorptive assays, including ELISA. In the classical HAI, even antibodies of relatively low affinity can demonstrate high titers, provided that the antibodies are present in the serum in large quantities.

In the SA-HAI with ELISA plates of the present invention, sera samples can be removed from the wells after incubation with the virus that is pre-attached to the plates and before application of erythrocytes. This actually triggers dissociation of lower affinity antibodies from the virus particles and removal of those antibodies from the reaction volume, which affects the observed titers.

SA-HAI experiments with and without post-incubation removal of the sera samples and washing wells with PBS/NaN$_3$ saline to examine the effects of low affinity Abs on the HAI titer showed that the difference between titers obtained in the two modes can, in general, be 2-5-fold, and even higher for some samples (FIG. 17; the titers obtained with sample removing and well washing are always lower). Notably, manipulations with the sample volumes do not affect the density of the viruses attached to the SA-HAI plates, as was demonstrated in separate ELISA tests (data not shown) Also important is that decreasing the virus density after washing the wells would increase the observed sera titers due to depletion of the agglutinating capacity in the wells; the effect opposite to what was observed in the experiments. Performing the SA-HAI assay with ELISA plates with and without removal of sera samples and washing wells can help to characterize the relative contribution of high- and low-affinity functional antibodies in the humoral immune response.

As stated above, hemagglutination (HA) and hemagglutination inhibition (HAI) functional assays remain important instruments of analysis of virus-cell interaction and efficacy of virus-specific antibodies and sera. However, the classical protocols of HA and HAI demonstrate limited sensitivity towards many viruses and require significant volumes of virus samples, erythrocytes, sera, and antibodies.

Embodiments of the present invention comprise a new method for the functional characterization of viruses and virus-specific antibodies and sera, the Surface-Assisted Hemagglutination/Hemagglutination Inhibition functional assay, the "SA-HA/HAI" assays. Embodiments of the present invention demonstrate sensitivity of the SA-HA assay to various influenza viruses about 7-200 times higher than the traditional HA, and sensitivity of the SA-HAI assay to influenza-specific antibodies about 10-50 times higher than in the traditional HAI, depending on the type of the virus and the type of erythrocytes used.

This enhancement in sensitivity allows analysis of low concentration experimental samples, and saves precious materials, such as convalescent sera and viruses. The SA-HA/HAI can use the same types of erythrocytes as the traditional HA/HAI: human, mammalian, and avian.

Performing the SA-HAI assay in the mode that uses ELISA plates allows determination of the relative contributions of low- and high-affinity functional antibodies in the HAI titer, which is technically impossible in the classical HAI assay. This makes the ELISA mode of the SA-HAI assay a valuable tool that can provide deeper insight into the quality of protective humoral immune responses.

The SA-HA/HAI assay results can be evaluated visually, in a manner similar to classical HA/HAI assays. However, visual evaluation lacks adequate precision for high-sensitivity experiments and it is prone to human errors, due to differences in perception of different operators. Photo-registration and digital processing of the SA-HA/HAI images increases the precision of the method and eliminates the subjectivity of visual evaluation. Introduction of the numerical Hemagglutination Parameter (HAP) that reflects the degree of agglutination in every well of the SA-HA or SA-HAI plate changes the analysis of the HA or HAI assays from a subjective visual evaluation to precise mathematical processing of titration curves.

Introduction of the advanced standardization concept using Linked Standard Dilution and Linked Hemagglutination Parameter of the standard significantly decreased the variability of the SA-HAI data. Image processing and computation of the SA-HA and SA-HAI titers can be performed in-line with photo registration and in real time. The SA-HA/HAI method can be performed in a high-throughput mode and allows automation.

EXAMPLES

In all the examples below, the major solvent used for all components of the assay, such as media, tested sera, antibody samples, viruses and erythrocytes was PBS saline containing 0.1% of sodium azide NaN$_3$ (PBS/NaN$_3$). Sodium azide was added to protect the saline from bacterial or yeast contamination.

Example 1

SA-HA/HAI Method Using Opsonized Plates

Protocol of the SA-HA/HAI using opsonized U-shaped 96-well plates (U-bottom 96-well format plate, clear polystyrene, Corning #3795).

Processing of Erythrocytes

Types of erythrocytes used in the SA-HA/HAI experiments were: human group O, turkey, chicken, guinea pig, horse. Human erythrocytes were acquired from Florida Blood Bank or via internal blood donations at Vaxdesign Corp. Turkey, chicken, guinea pig and horse erythrocytes were purchased from Rockland Immunochemicals as suspensions in citrate buffer.

Aliquotting and Storage

The erythrocytes were aliquotted immediately after receiving by 1.0 mL in microfuge vials and stored at 4° C. until further use. The normal storage time was no longer than 3 weeks for human, turkey, horse and chicken erythrocytes, and no longer than 1 week for guinea pig erythrocytes.

Washing and Re-Suspending a. The vial containing the erythrocytes was centrifuged (600 g, 2 min).
b. The supernatant+the top layer of the cells were aspirated carefully using a 1-mL pipette. PBS/$NaN_3$ (1 mL) was added to the pellet. The cells were re-suspended by slow back-and-forth pipetting.
c. Steps a-b were repeated.
d. The cells were again centrifuged (600 g, 2 min). The supernatant+the top layer of the cells were aspirated using a 1-mL pipette, and after that 1 mL of 0.5% BSA in PBS/$NaN_3$ was added to the pellet. The cells were re-suspended by slow back-and-forth pipetting, taking care to produce no bubbles.
e. The cells were again centrifuged (900 g, 5 min). The supernatant+the top layer of the cells were aspirated using a 1-mL pipette. The residual pellet represented the 100% HCT stock. Typically, the final pellet constituted ~½ to ~¼ of the initial quantity of the erythrocytes.
f. The pellet was stirred slowly to make it homogeneous. An appropriate aliquot of the pellet was suspended in 0.5% BSA in PBS/$NaN_3$. Unless otherwise specified, the final concentration should be 0.05% HCT for human, horse and turkey erythrocytes and 0.025% HCT for guinea pig erythrocytes.

The processing of erythrocytes described above was performed anew for each day of experiments. Any leftovers of the processed erythrocytes were disposed of after the experiment.

Processing of the Virus

The following BPL-inactivated virus standards were obtained from the U.S. Centers for Disease Control and Prevention, Atlanta, Ga. (CDC):

A/Brisbane/59/2007 [H1N1]
A/New Calcdonia/20/99 [H1N1]
A/Solomon Islands/3/2006 [H1N1]
A/Wisconsin/67/2005 [H3N2]

These virus samples were stored undiluted in 1.5-mL microfuge vials at 4° C. During the processing, the microfuge vial with the virus was stirred vigorously in a bench vortex for 30 s; no sonication was used. Afterwards, the vial was centrifuged (400 g, 5 min). The necessary aliquot of the supernatant was taken out and diluted in 0.5% BSA/PBS/$NaN_3$. This processing was performed anew for each day of experiments.

BPL-Inactivated Virus Standard of a/California/7/2009 [H1N1] from the CDC or American Type Culture Collection (ATCC)

Due to the increased instability of the A/California/7/2009 [H1N1] virus sample, it was aliquotted immediately after receiving in 0.5-mL portions, frozen and stored at −80° C. until further use. For a serial of the SA-HA/HAI experiments, a frozen aliquot of this virus was thawed at room temperature and diluted in 4 mL of PBS/$NaN_3$ saline. The diluted sample was sonicated on ice using Sonic Dismembrator, Model 500 from Fisher Scientific, catalog #15-338-550 at 12% power level, five times for 50 s. After sonication, 0.5 mL of 99% glycerin was admixed to the solution. Afterwards, the virus solution was further aliquotted by 0.25 mL, and those secondary aliquots were either used immediately or frozen and stored at −80° C. for further use. After thawing, those secondary aliquots could be used immediately without further processing.

Influenza Viruses in Mice Allantoic Fluids:

The following influenza viruses in mice allantoic fluids were obtained from Sanofi Pasteur:

A/Brisbane/59/2007 [H1N1]
A/New Calcdonia/20/99 [H1N1]
A/Solomon Islands/3/2006 [H1N1]
A/Wisconsin/67/2005 [H3N2]
B/Malaysia/2506/2004
B/Florida/4/2006

Due to instability of the agglutinating capacity of these samples, they were aliquotted into 0.05 mL portions immediately after receiving, frozen and stored at −80° C. until further use. Before the experiment, the aliquots were thawed at room temperature, diluted as necessary in PBS/$NaN_3$ and used immediately on the same day.

Typical SA-HA Experiment Using Opsonized Plates

For most SA-HA experiments, the plate layout was horizontal (i.e., the placement and serial dilution of the samples performed from left to right).

Blocking/Opsonization of the Plate

The plate was filled with 2% BSA in PBS/$NaN_3$, 160 μL per well, and incubated at 4° C. in a planar plate shaker, ~600 rpm for at least 40 min.

Pre-Filling with Media

The plate was flicked off and tapped upside down on a clean paper towel. The plate was filled with 0.5% BSA in PBS/$NaN_3$, 40 μL per well.

Filling with Virus

Unless specified otherwise, the virus initial dilution was 1:50 or 1:100.

Pre-diluted virus was added to the wells of the column 1, 40 μL per well, thus becoming diluted 2 times. Dual serial dilutions of the virus were made from left to right, from the column 1 to the column 11 using an 8-channel 200-μL pipetter and transferring by 40 μL per channel in every pass. Back-and-forth pipetting in each column was used to mix solutions properly, not less than six pipettings per pass, producing no bubbles. The last 40-μL portion taken from the column 11 was discarded. The column 12 contained no virus.

Adding Solution 0.5% BSA in PBS/$NaN_3$ was added to all the wells, 40 μL per well, not touching the menisci. For this, the pipette tips were leaned on the top part of the well.

Mixing in a Planar Plate Shaker

The plate was placed in the plate shaker, such as Digital mini vortexer IKA MS3 from IKA Works, Wilmington, N.C., and a short (~5 s) mixing at 1000 rpm was performed three times. After mixing, erythrocytes were added.

Filling with Erythrocytes and Incubation

Erythrocytes processed and diluted as described above were added to all the wells, 40 µL per well, the plate was again subjected to short mixing in the plate shaker at 800 rpm, and then incubated with shaking at 500 rpm for 30 min. Afterwards, the plate was left still on the bench for 2-4 h, depending on the type of erythrocytes used in the assay, to allow erythrocytes to precipitate and form the hemagglutination patterns.

Plate Reading

The plate could be read and analyzed visually, or using photo-registration in a short-focus photo reader, such as an ELISPOT plate reader, AID ELR04 AID GmbH, Germany, with subsequent digital processing of the patterns of hemagglutination, as described above, and the SA-HA titer determined as a midpoint of the HA titration (FIG. 7).

Typical SA—HAI Experiment Using Opsonized Plates

For most SA-HAI experiments, the plate layout was vertical (i.e., the placement and serial dilution of the samples were performed from the row A to the row H of the plate).

The virus titer determined in the previous SA-HA assay was used to calculate the virus dilution to be used in the SA-HAI assay:

$$(\text{SA-HAI assay virus dilution}) = (\text{SA-HA titer})/4 \qquad (2)$$

Blocking of the Plate

As described above for the typical SA-HA assay.

Pre-Filling with Media

As described above for the typical SA-HA assay.

Filling with Sera or Antibody Solutions

Pre-dilutions of the tested sera were usually from ~1:100 to ~1:800, depending on the expected immune response. Pre-dilutions of MIMIC® samples were usually ~1:1 to ~1:10, depending on the expected antibody levels.

Pre-diluted sera or MIMIC® samples were placed in the wells of the row A, 40 µL per well. Dual serial dilutions of the samples were performed from row A to row G or H using a 12-channel 200-µL pipetter by transferring 40 µL from the wells of the previous row to the next row. The technique of the dilution is the same as described above for the typical SA-HA assay.

Adding Virus

Virus diluted according to the results of the SA-HA test as specified above was added to all the wells, 40 µL per well, except for the No Virus negative control wells, without touching the menisci. For this, the pipette tips were leaned on the top part of the wells.

Mixing with a Planar Plate Shaker.

As described above for the typical SA-HA assay.

Incubation with Virus

The plate was incubated in the planar shaker at 4° C. (refrigerator) or at room temperature (on the bench) at 500 rpm, covered, for ~1-2 h, depending on the virus type. After the incubation, erythrocytes were added.

Filling the Plates with Erythrocytes and Incubation

As described above for the typical SA-HA assay.

Plate Reading

As described above for the typical SA-HA assay. The digital processing of the hemagglutination patterns is described in details above.

Example 2

SA-HA/HAI Method Using ELISA Plates

Protocol of the SA-HA/HAI assays using ELISA U-shaped 96-well plates (Immulux HB from Dynex, catalog #1011 or ImmunoGrade BRANDPlates from BrandTech Scientific, catalog #781724).

Processing of Erythrocytes

As described above, in Example 1.

Processing of the Viruses

The processing was similar to the described above in the Example 1 for the SA-HA/HAI assays with opsonized plates, except that the final solvent used for viruses before application to the plates was BSA/NaN$_3$ saline.

Typical SA-HA Experiment Using ELISA Plates

For most SA-HA experiments, the plate layout was horizontal (i.e., the placement and serial dilution of the samples performed from left to right).

Pre-Filling with Saline

All the wells were filled with PBS/NaN$_3$, 50 µL per well.

Filling with Virus

The filling and serial dilution techniques and the typical layouts were similar to that described above in the Example 1, the protocol for SA-HA/HAI using opsonized plates. The filling aliquots were 50 µL per well.

Attaching Virus to the Plate

The plate was incubated overnight at 4° C. (refrigerator), on a planar plate shaker at ~500 rpm.

Blocking

The plate was flicked off and tapped upside down on a clean paper towel, filled with 2% BSA in PBS/NaN$_3$, 200 µL per well, and incubated at 4° C. on a planar plate shaker, ~400 rpm for at least 2 h.

Filling with Erythrocytes and Incubation

Erythrocytes diluted in the (0.25% BSA+0.25% OVA)/PBS/NaN$_3$ were added by 50 µL per well. Typical concentrations of erythrocytes were 0.01-0.025% HCT. Afterwards, the plate was left still on the bench for ~2-4 h., depending on the type of erythrocytes, to allow erythrocytes to precipitate and form the hemagglutination patterns.

Plate Reading

As described in Example 1.

Typical SA-HAI Experiment Using ELISA Plates

For most SA-HAI experiments, the plate layout was vertical (i.e., the placement and serial dilution of the samples performed from top to bottom).

The virus titer determined in the SA-HA assay is used to calculate the virus dilution to be used in the SA-HAI assay as shown in the formula (2) above.

Filling with Virus

The plate was filled with the virus chosen for the experiment and diluted according to the results of the previously set SA-HA test in PBS/NaN$_3$, 50 µL per well.

Attaching Virus to the Plate

As described above.

Blocking the Plate

As described above.

Pre-Filling with Media

The plate was flicked off and tapped on a clean paper towel, and filled with (0.25% BSA+0.25% OVA)/PBS/NaN$_3$, 50 µL per well.

Filling with Sera or Antibody Solutions

The conditions and technique for placement and serial dilution of the tested sera or antibody solutions was similar to that described in Example 1 for the typical SA-HAI experiment with opsonized plates, except that:

a. The solvent for the samples was (0.25% BSA+0.25% OVA)/PBS/NaN$_3$ b. The aliquot volume was 50 µL.

Incubation with Sera or Antibody Samples

As described above for Example 1 with the opsonized plate.

Optional Emptying of the Plate and Washing, or Preserving of the Sample without Washing There are two different versions of the SA-HAI assay with ELISA plates: with and without emptying and washing the plate with PBS/NaN$_3$. The specific features and difference between the two versions are described above.

Emptying was performed by flicking the plate off and tapping on a clean paper towel. Washing was performed with PBS/NaN$_3$, 200 µL per well, using an 8- or 12-channel 200-µL pipetter.

Adding Erythrocytes, No Emptying/No Washing Version.

Erythrocytes at a concentration 10 times higher than the desired final concentration were added by 5.01 µL to the wells containing 50-µL samples well by squirting from a 12-channel 200-µL pipetter. The volumes were squirted in the wells rather than slowly squeezed out. The pipetter was washed with PBS/NaN$_3$ before every addition of erythrocytes to every row. After adding erythrocytes to all wells, the plate was subjected to short mixing via the planar plate shaker. Typical final concentrations of erythrocytes were ~0.01-0.025% HCT.

Adding Erythrocytes, Emptying/Washing Version.

a. After emptying/washing, the plate was filled with (0.25% BSA+0.25% OVA)/PBS/NaN$_3$ solution, 50 µL per well, and the erythrocytes added in the manner described above.

b. Alternatively, the emptied/washed plate was filled with erythrocytes diluted to the final concentration of ~0.01-0.025% HCT, 50 µL per well.

Final Incubation with Erythrocytes

The plate was kept still and covered on the bench for ~2-4 h, depending on the type of erythrocytes used in the assay to allow erythrocytes to precipitate and form the hemagglutination patterns.

Plate Reading

As described in Example 1.

Example 3

Classical HA/HAI Assay

The protocol for the classical HA/HAI assays were versions of the HA/HAI protocols updated by Hierholzer et al. (1969) *Applied Microbiol.* 18, 824-833. A few details of the assay are important:

The major solvent used for dilution of virus samples, sera, antibody samples and erythrocytes was PBS/NaN$_3$ saline.

The protocols for processing of erythrocytes and viruses remained the same as described above, except that only PBS/NaN$_3$ saline was used as a solvent or diluent in all cases and on all stages of the procedures.

Figure 8:
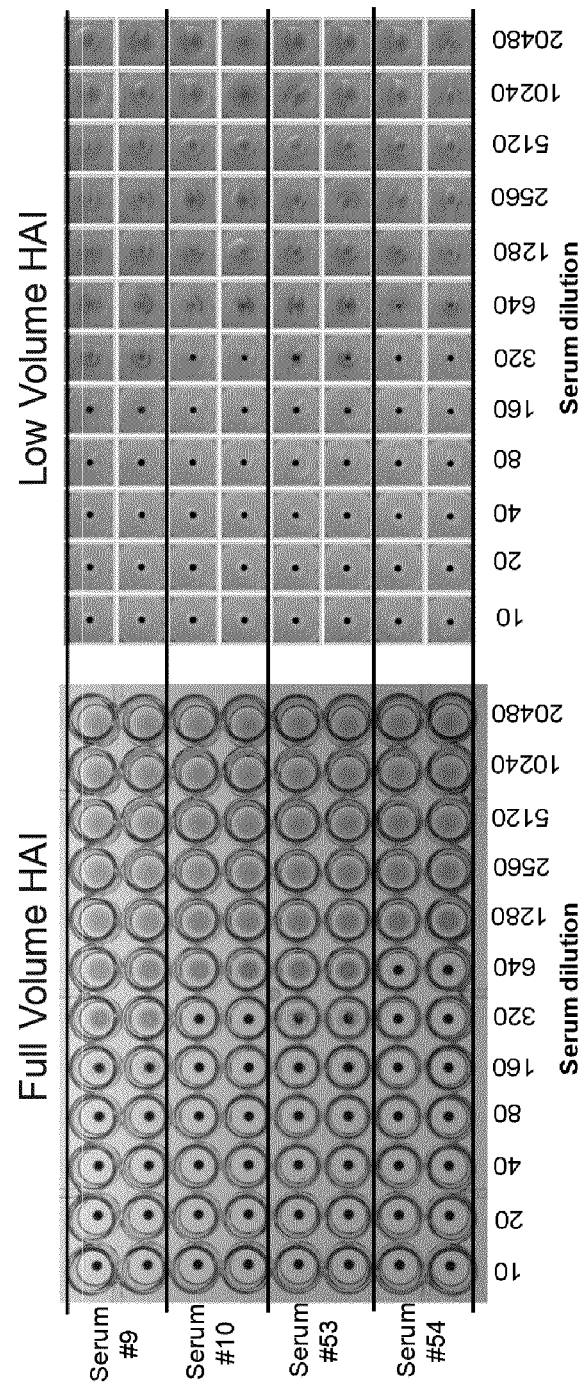

The classical HA and HAI assays were performed in two functionally equivalent modes: Full Volume Mode and Low Volume Mode, which used 30-50-µL filling aliquots in the U-bottom plates and 7-µL filling aliquots in the V-bottom plates, respectively. Both modes gave equivalent results concerning HAI titers for the tested sera (FIG. 8). Low Volume Mode was developed to allow comparative experiments with scarce virus and sera samples.

The final concentration (after adding to the wells and mixing) of erythrocytes used in the classical HA/HAI assays was maintained at 0.5% HCT.

Classical HA Assay

For most HA assays, we used a horizontal layout (i.e., the serial dilution of the tested virus was performed from left to right).

Typical starting pre-dilution of the virus samples were 1:5 or 1:10.

a. The plate was filled with the filling aliquots of PBS/NaN$_3$ saline (30-50-µL in the Full Volume Mode or 7-µL in the Low Volume Mode).

b. One filling aliquots of the pre-diluted virus were added to the wells of Column 1.

c. Dual serial dilution was performed from Column 1 to Column 11 using an 8-channel 200-µL pipetter. The last portion taken from Column 11 was discarded.

d. One filling aliquot of PBS/NaN$_3$ saline was added to all wells.

e. One filling aliquot of erythrocytes at 1.5% HCT in PBS/NaN$_3$ saline was added to all wells, and a short mixing was performed in a planar plate shaker.

f. The plate was incubated still on the bench for ~30-60 min in the Full Volume Mode, or ~15-30 min in the Low Volume Mode, depending on the type of erythrocytes, to allow formation of the hemagglutination patterns (buttons and halos).

g. In the Full Volume Mode, the plate was read visually, and the HA titer was determined as a borderline between the halo and button area, left to right. In the Low Volume Mode, the plate was read visually as described above, or using photo registration, digital image processing, and computation of the HA titer, as described above.

Classical HAI Assay

For most HAI assays, we used a vertical layout (i.e., the serial dilution of the tested sera was performed from the row A to the row G or H of the plate). The virus titer determined in the HA assay was used to calculate the virus dilution to be used in the HAI assay as shown in the formula (2) above.

Typical starting pre-dilutions of the tested sera samples were 1:5 or 1:10. MIMIC® samples were not tested using the classical HAI assay due to lack of sensitivity.

a. The plate was filled with the filling aliquots of PBS/NaN$_3$ saline (30-50-µL in the Full Volume Mode or 7-µL in the Low Volume Mode).

b. Filling aliquots of the tested sera samples were added in the wells of row A.

c. Dual serial dilution from Row A to Row G or H was performed using a 12-channel 200 µL pipetter. The last portion taken from Row G or Row H was discarded.

d. One filling aliquot of the virus pre-diluted to the started concentration as specified above was added to all of the wells, except for the negative control No Virus wells, and a short mixing was performed in a planar plate shaker.

e. The plate was incubated for ~1 h on the bench in the planar plate shaker at 400-600 rpm.

f. One filling aliquot of erythrocytes at 1.5% HCT was added to all wells, and a short mixing was performed in a planar plate shaker.

g. The plate was incubated still on the bench for ~30-60 min in the Full Volume Mode, or ~15-30 min in the Low Volume Mode, depending on the type of erythrocytes, to allow formation of the hemagglutination patterns (buttons and halos).

h. In the Full Volume Mode, the plate was read visually, and the HA titer was determined as a borderline between the halo and button area, left to right. In the Low Volume Mode, the plate was read visually as described above, or using photo registration, digital image processing, and computation of the HA titer, as described above.

Example 4

Comparison of the Classical HAI and SA-HAI Performed with Human Erythrocytes A panel of 30 pre- and post-vaccination sera from 15 donors immunized for influenza in the season 2007/2008 was tested in the classical HAI assay and the SA-HAI assays/opsonized plates using human group O erythrocytes. The classical HA/HAI assays and the SA-HA/HAI assays were performed as specified above. In the classical HAI assay, sera samples were tested in quadruplicate, and in the SA-HAI assay in duplicates. The virus used in the experiment was A/Solomon Islands/3/2006 [H1N1], BPL-inactivated standard from CDC. The final concentration of human erythrocytes in the wells of the classical HAI was 0.5% HCT, and the final virus dilution in the wells was 1:120. For the SA-HAI, the corresponding numbers were 0.017% HCT and 1:12000. The comparison of the classical HAI and SA-HAI with opsonized plates and human erythrocytes is presented in FIG. 9 and in the data table presented with the figure. Correlation between the two methods was good, and the SA-HAI demonstrated sensitivity enhancement ~23-fold over the classical method, as seen from the averaged titer ratio presented in the data table and from the slope of the correlative scattered plot (FIG. 9).

Example 5

Comparison of the Classical HAI Performed with Human Erythrocytes and SA-HAI Performed with Turkey Erythrocytes Comparative experiments similar to those described above were performed using the SA-HAI protocols with opsonized plates and turkey erythrocytes. The final concentrations of the erythrocytes and the virus used were the same as above. The results are presented in FIG. 10 and in the data table presented with the figure.

In this case, as in the previous example, the correlation between the two methods was good, and the SA-HAI assay demonstrated sensitivity enhancement ~21-27-fold versus the classical method, as seen from the averaged titer ratio and from the slope of the correlative scattered plot.

Example 6

Comparing Classical HAI Titers Determined with Human Erythrocytes and SA-HAI Titers Using Guinea Pig Erythrocytes Pre- and post-vaccination sera from three donors immunized for influenza in the season 2007/2008 were tested in the classical HAI assay using human group O erythrocytes and the SA-HAI assay with opsonized plates using guinea pig erythrocytes, as specified above. The virus was A/Solomon Islands/3/2006 [H1N1], BPL-inactivated standard from CDC. The final concentration of guinea pig erythrocytes and final virus dilutions in the SA-HAI assay were 0.0083% HCT and 1:10000, respectively. The results presented in FIG. 11 and in the data table presented with the figure demonstrated good correlation with the classical HAI method and sensitivity enhancement of ~30-50-fold, judged from the averaged titer ratio and from the slope of the correlative scattered plot.

Example 7

Comparing Classical HA Titers and SA-HA Titers for Influenza Viruses in Allantoic Fluids The classical HA assay was performed in Low Volume mode, as described above, and the SA-HA assay was performed with ELISA plates in the year 2010 using virus samples in mice allantoic fluids, as listed above. The results presented in FIG. 12 and in the data table placed beside the figure demonstrate ~7- to ~200-fold enhancement of sensitivity in the SA-HA assay versus the classical HA assay, depending on the virus type.

Example 8

Comparing Classical HAI and SA-HAI Titers Using Turkey Erythrocytes and H1N1 Influenza Virus in Allantoic Fluids The classical HAI assay was performed in Low Volume mode, as described above, and the SA-HAI assay was performed with ELISA plates in the year 2010 using virus samples in mice allantoic fluids. The virus was A/Brisbane/59/2007 [H1N1]. The final concentration of turkey erythrocytes and final virus sample dilution in the SA-HAI assay were 0.025% HCT and 1:5280. The results presented in FIG. 13 and in the data table placed beside the figure demonstrate good correlation between the two assays and a sensitivity enhancement of ~7-fold, judged from the averaged titer ratio and from the slope of the correlative scattered plot.

Example 9

Comparing Classical HAI and SA-HAI Titers Using Turkey Erythrocytes and H3N2 Influenza Virus in Allantoic Fluid The classical HAI assay was performed in Low Volume mode, as described above, and the SA-HAI assay was performed with ELISA plates in the year 2010 using virus samples in mice allantoic fluids. The virus was A/Wisconsin/67/2005 [H3N2]. The final concentration of turkey erythrocytes and final virus dilution in the SA-HAI assay were 0.025% HCT and 1:1600. The results presented in FIG. 14 and data table placed beside the figure demonstrate a sensitivity enhancement of ~30-fold, judged from the averaged titer ratio. Low numbers of available samples did not allow building a comprehensive dual scattered plot as in the previous experiments.

Example 10

SA-HAI Analysis of Cross-Protection Against Swine Flu with Seasonal Influenza Vaccine 2009/2010

Sera from 27 donors immunized with anti-influenza Fluvirin vaccine in season 2009/2010 were tested using SA-HAI assay with opsonized plates and turkey erythrocytes. The H1 component of Fluvirin vaccine was derived from the A/Brisbane/59/2007 [H1N1] virus. The objective of the study was to estimate the capacity of the seasonal vaccine to protect from the newly appeared pandemic threat of A/California/7/2009 [H1N1] Swine Flu virus. Accordingly, the SA-HAI assays of the donor sera were performed using A/Brisbane/59/2007 [H1N1] and A/California/7/2009 [H1N1] BPL-inactivated virus standards from the CDC, in the opsonized plate mode.

Figure 15A:
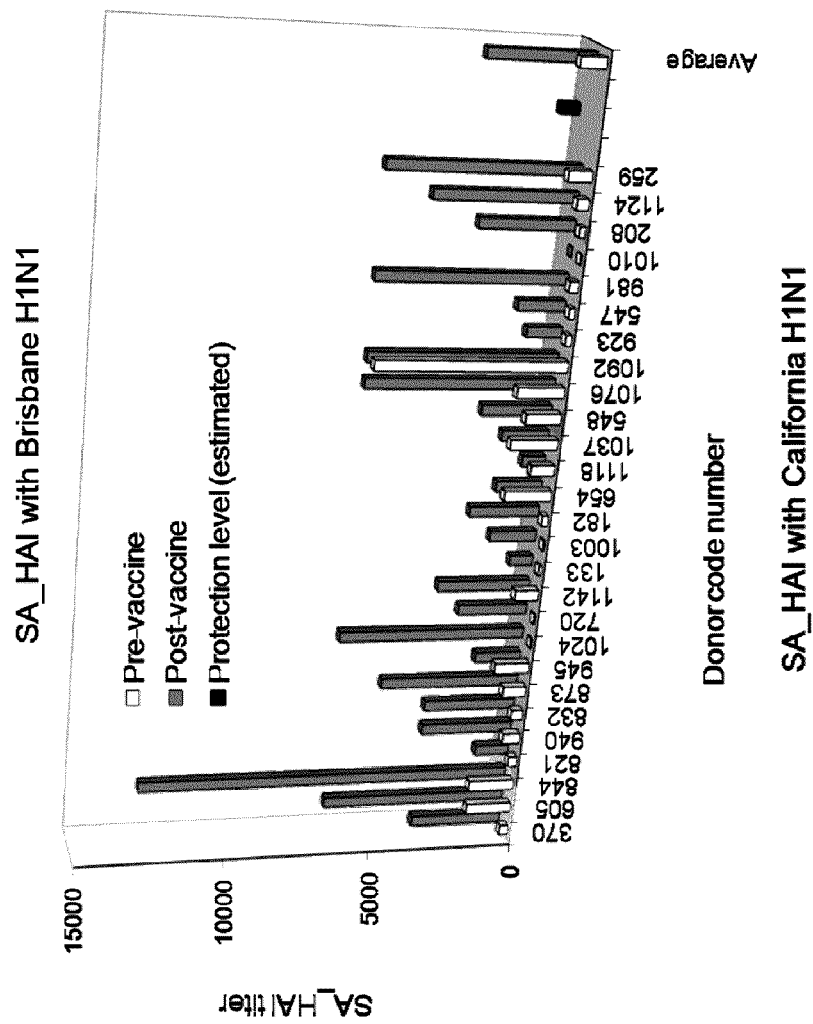
Figure 15B:
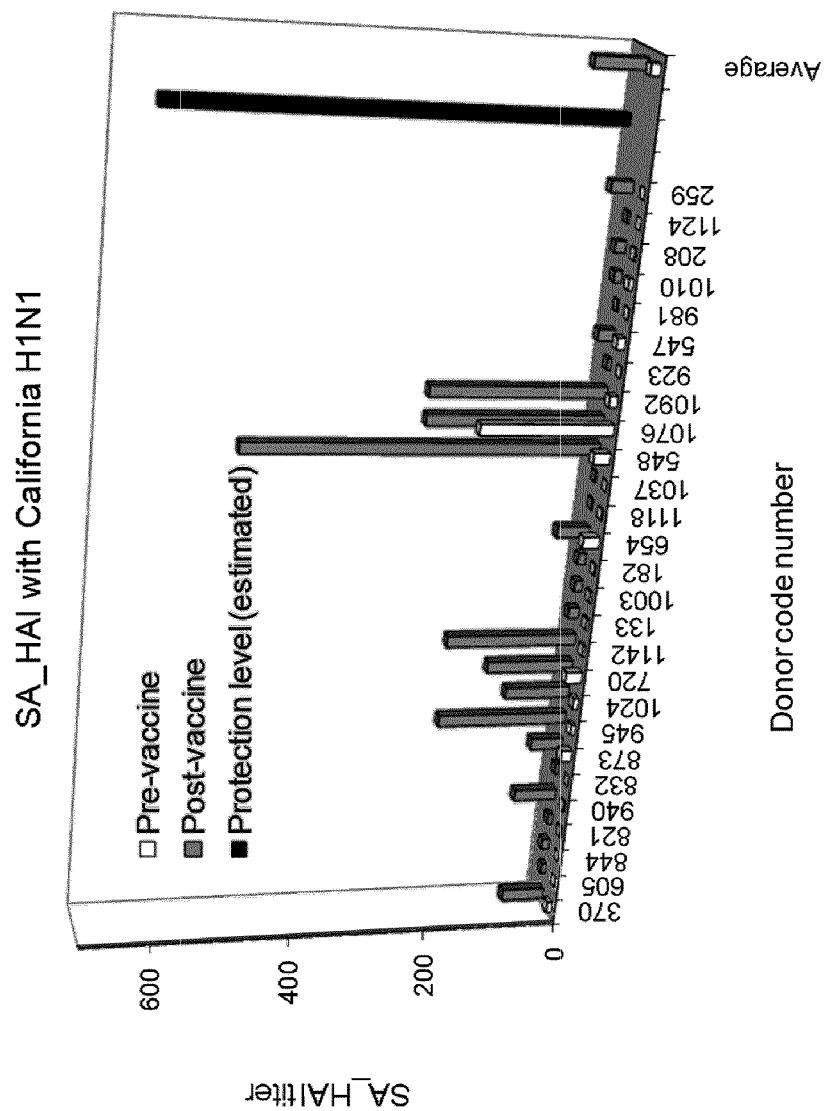

The results of sera screening are shown in FIG. 15. While the efficacy of the vaccine against the seasonal virus was high, as can be seen by the difference between the pre- and post-vaccine titers, the cross-activity of the immunized sera against the new Swine Flu virus was significantly lower the level that is required for protection. The protection level for SA-HAI titers was estimated ~640 to compare with the level ~64 accepted for the classical HAI assays. The estimated sensitivity enhancement of the assay towards the classical HAI was ~10 (data not shown).

Thus, seasonal vaccination would not be expected to protect from infection, although perhaps it could alleviate the severity of the illness, a conclusion that confirmed the results of internal studies performed at the CDC (Hancock et. al. (2009) *N. Engl. J. Med.* 2009, 361, 1945-1952).

Example 11

SA-HAI Analysis of Samples from In Vitro MIMIC® Setups Immunized with Vaccine and Recombinant Antigen MIMIC® setups based on immune cells from human donors were immunized in vitro with Fluvirin-2010 seasonal vaccine and with recombinant H1 hemagglutinin originated from A/California/7/2009 [H1N1] "Swine Flu" virus (Protein Sciences, Meriden, Conn.). The MIMIC® supernatants were tested with SA-HAI assay using ELISA plates. The results of the screening in FIG. 16 demonstrate significant increase of virus-specific and potentially neutralizing antibodies after vaccination, in comparison with the No Antigen samples. At the same time, challenging the MIMIC® system with vaccine generally demonstrated higher efficacy than challenging with the recombinant antigen, which may have been due to the effective adjuvant used in the vaccine formulation.

Example 12

Testing Affinity Profile of Potentially Protective Antibodies in Human Sera and MIMIC® Samples with SA-HAI Assay Sera from donors immunized with Fluvirin in season 2009/2010 and a sample from MIMIC® system challenged with various influenza antigens were tested for relative contribution of high and low affinity antibodies in the HAI titer. The virus used in the assay was A/Brisbane/59/2007 [H1N1], BPL-inactivated standard from the CDC. Data presented in FIG. 17 demonstrate significant impact of low affinity antibodies in the assays where sera samples were not removed from the SA-HAI plate after incubation over the pre-attached virus, and the wells were not washed. Relative contribution to the SA-HAI titers from the antibodies that defied dissociation from the virus during removal of the sera samples and washing was never larger than 30%, as judged from comparison of the titers determined for the wells where samples were removed and the wells washed and the wells where samples were not removed.

The experiment demonstrates the importance of affinity profiling for potentially protective antibodies elicited by vaccination. High HAI titers do not necessarily manifest high protective capacity. Washing of the wells with $PBS/NaN_3$ does not decrease the density of the pre-attached viruses (checked using virus-specific ELISA; data not shown). Also, it is easy to demonstrate that decreased virus density after washing the wells would increase the observed sera titers due to depletion of the agglutinating capacity in the wells; the opposite of what was observed in the experiments.

All documents, publication, manuals, article, patents, summaries, references and other materials cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

The invention claimed is:

1. A method for determining functional binding activity of an antibody, comprising:
(a) incubating an agglutinating factor in an activated well of a culture plate under conditions achieving attachment of the agglutinating, factor to a surface of the well bottom,
(b) adding an antibody to the well of (a),
(c) adding a target object to the well of (b) under conditions permitting agglutination of the target object by the agglutinating factor, and
(d) detecting agglutination of the target object on the surface of the well bottom of (c), wherein when agglutination detected in (d) is less than agglutination detected in the absence of the antibody, the antibody is determined to have functional binding activity.

2. The method of claim 1, further comprising washing the well of the plate of (c) with a buffered wash solution after adding the antibody to the well.

3. The method of claim 1, further comprising adding a blocking agent to the well of (a), prior to adding the antibody.

4. The method of claim 1, wherein agglutination is detected by quantifying two-dimensional agglutination patterns created by the agglutinated target objects on the surface of the well bottom of the plate.

5. The method of claim 1, wherein the agglutinating factor is a factor selected from the group consisting of a virus, a virus-like particle, a bacterium, and a protein.

6. The method of claim 1, wherein the agglutinating factor is a virus.

7. The method of claim 1, wherein the target object is cells or microspheres.

8. The method of claim 7, wherein the microspheres are latex microspheres coated with a receptor that binds with the agglutinating factor.

9. The method of claim 7, wherein the cells are cells selected from the group consisting of erythrocytes, lymphocytes, epithelial cells, and endothelial cells.

10. The method of claim 9, wherein the erythrocytes are avian erythrocytes or mammalian erythrocytes.

11. The method of claim 9, wherein the cells are erythrocytes present at a concentration of below 0.1% hematocrit.

12. The method of claim 9, wherein the lymphocytes are avian lymphocytes or mammalian lymphocytes.

13. The method of claim 1, wherein the plate comprising an activated well is an ELISA plate.

14. The method of claim 4, wherein the quantification of two-dimensional patterns is performed using digital photo registration and digital image processing.

15. The method of claim 2, further comprising determining a relative contribution of high affinity antibodies to the agglutination detected in (d) by comparing the value detected in (d) to a value detected in (d) where the well was not washed with a buffered wash solution after adding the antibody to the well.

16. The method of claim 1, wherein the antibody is added to the well as serum comprising the antibody.

17. The method of claim 1, wherein agglutination is detected at a sensitivity increased by at least about 10 times compared to performing the method in a non-activated well under conditions that provide agglutination in the well volume rather than on the surface of the well bottom.

* * * * *